United States Patent
Gurkan et al.

(10) Patent No.: US 11,376,590 B2
(45) Date of Patent: Jul. 5, 2022

(54) DIAGNOSTIC SYSTEM FOR HEMOGLOBIN ANALYSIS

(71) Applicant: CASE WESTERN RESERVE UNIVERSITY, Cleveland, OH (US)

(72) Inventors: Umut Gurkan, Shaker Heights, OH (US); Arwa Fraiwan, University Heights, OH (US); Peter Galen, Portland, OR (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 341 days.

(21) Appl. No.: 16/780,602

(22) Filed: Feb. 3, 2020

(65) Prior Publication Data

US 2020/0246794 A1    Aug. 6, 2020

Related U.S. Application Data

(60) Provisional application No. 62/800,137, filed on Feb. 1, 2019.

(51) Int. Cl.
*B01L 3/00* (2006.01)
*G01N 33/72* (2006.01)

(52) U.S. Cl.
CPC ........ *B01L 3/50273* (2013.01); *G01N 33/723* (2013.01); *B01L 2200/025* (2013.01); *B01L 2300/041* (2013.01); *B01L 2300/0663* (2013.01); *B01L 2400/0421* (2013.01)

(58) Field of Classification Search
None
See application file for complete search history.

(56) References Cited

U.S. PATENT DOCUMENTS

| 6,136,171 A | 10/2000 | Frazier et al. |
| 7,625,760 B2 * | 12/2009 | Kitaguchi ............... B01L 3/523 422/562 |
| 2017/0227495 A1 * | 8/2017 | Gurkan ............ G01N 27/44721 |

OTHER PUBLICATIONS

Applicant: Case Western Reserve University; International Application No. PCT/US20/20830, filed Mar. 3, 2020; PCT International Search Report and Written Opinion, Authorized Officer: Lee young; dated May 26, 2020; 6 pgs.

* cited by examiner

*Primary Examiner* — Matthew D Krcha
(74) *Attorney, Agent, or Firm* — Tarolli, Sundheim, Covell & Tummino LLP

(57) ABSTRACT

A diagnostic system detects and/or measures hemoglobin variants in blood of subject, such as HbA1c, to determine blood glucose concentration in the subject.

20 Claims, 16 Drawing Sheets

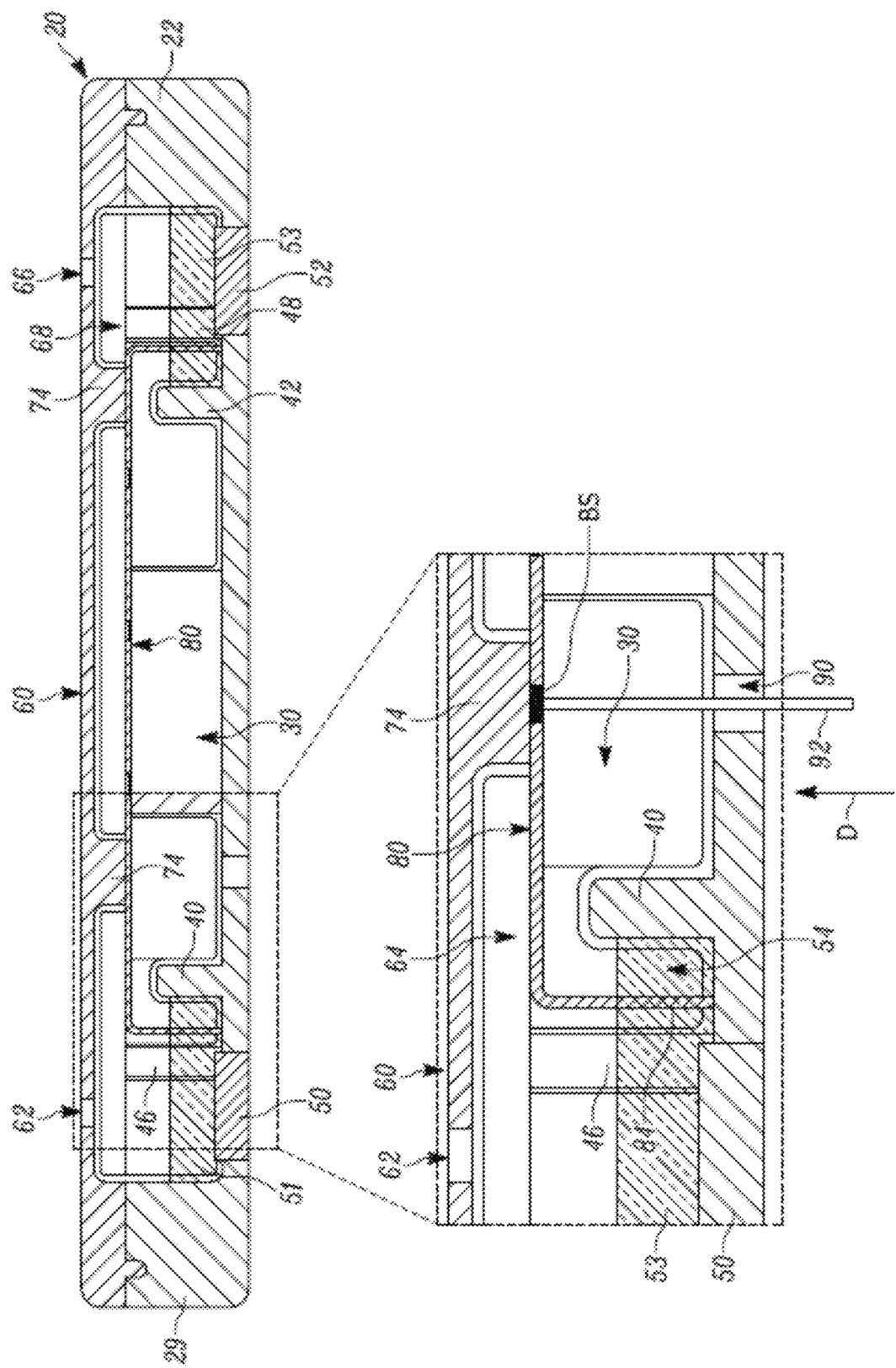

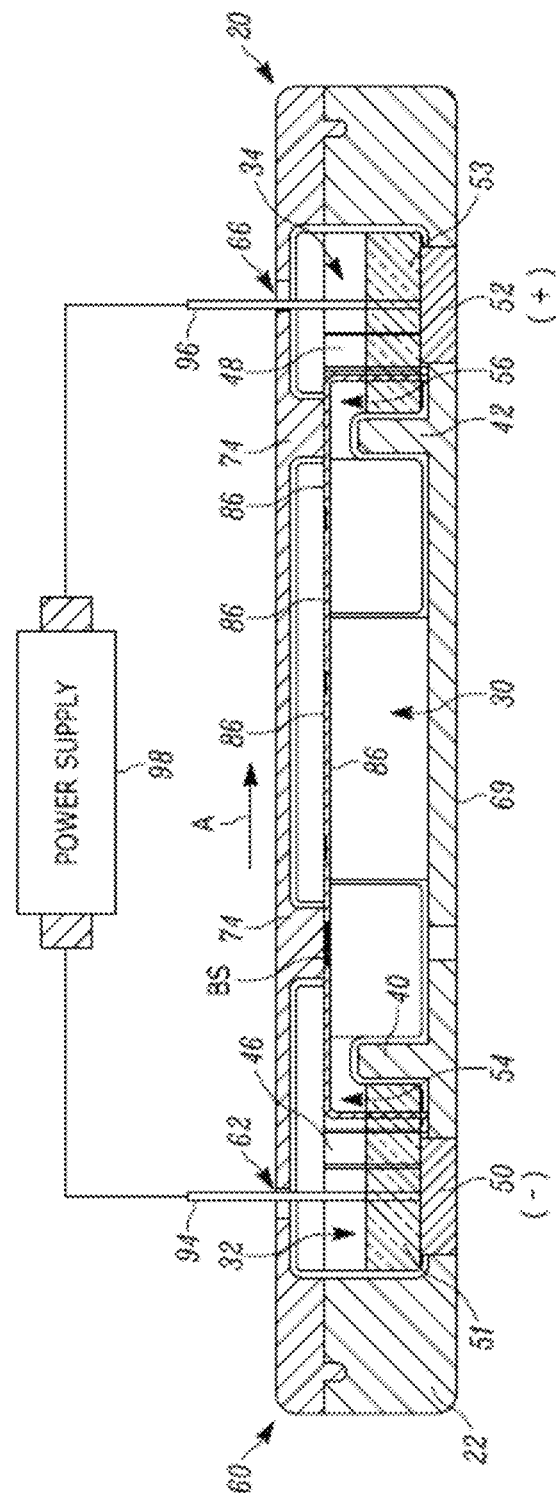

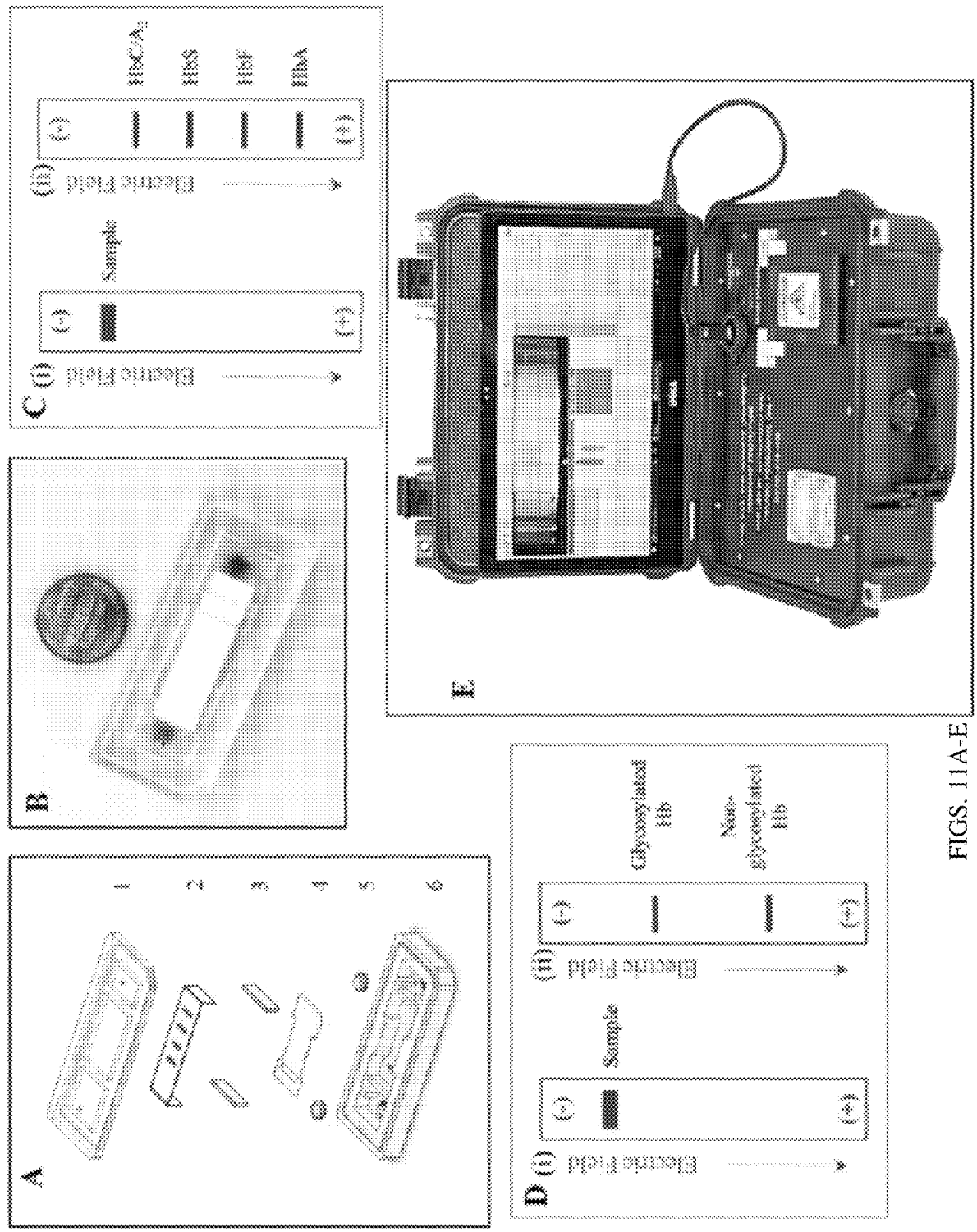
FIGS. 11A-E

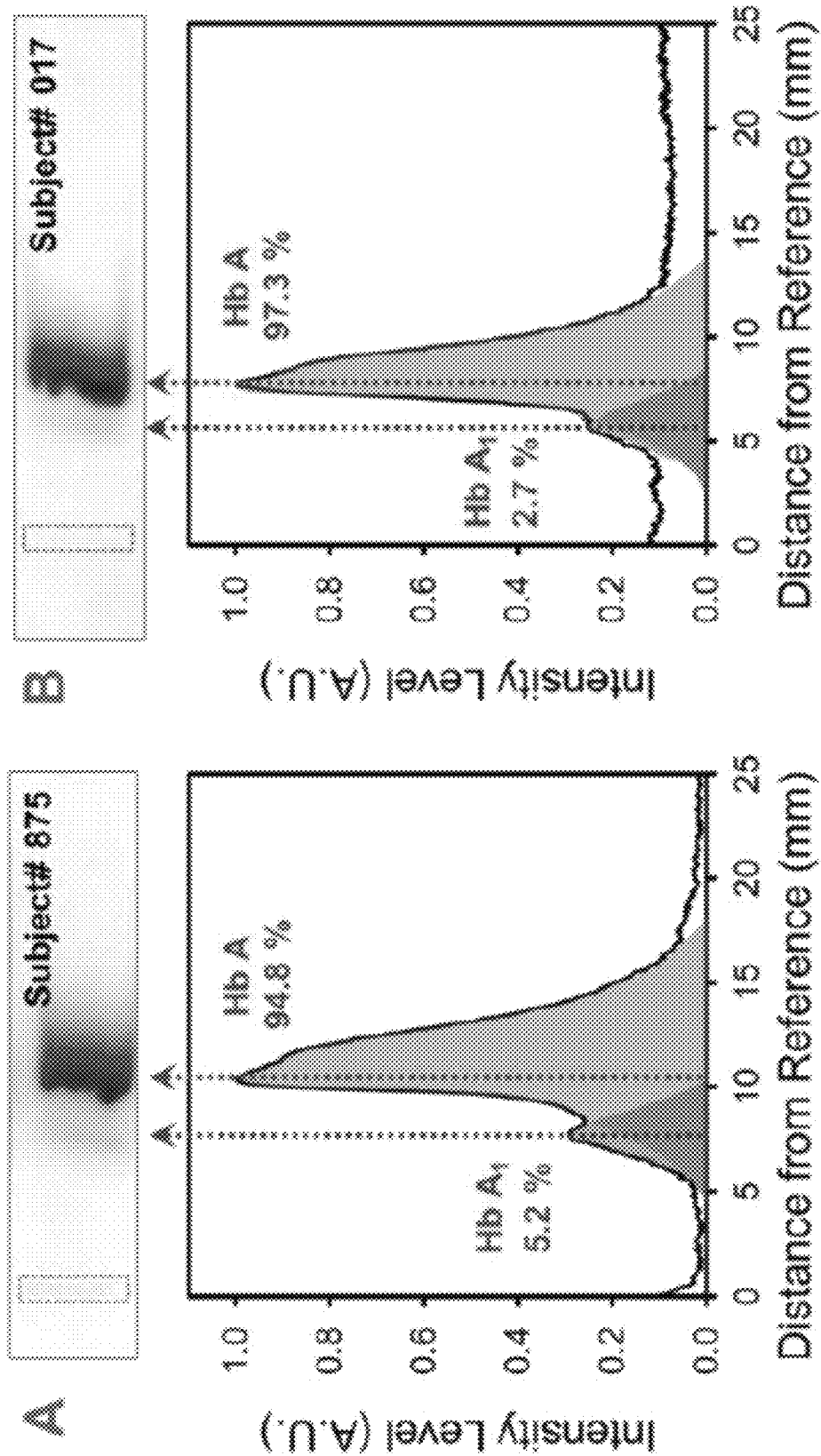
FIGS. 12A-B

DIAGNOSTIC SYSTEM FOR HEMOGLOBIN ANALYSIS

RELATED APPLICATION

This application claims priority from U.S. Provisional Application No. 62/800,137, filed Feb. 1, 2019, the subject matter of which are incorporated herein by reference in their entirety.

GOVERNMENT FUNDING

This invention was made with government support under Grant Nos. DK119048, awarded by The National Institutes of Health. The government has certain rights in the invention.

FIELD OF THE INVENTION

The present invention is related to a diagnostic system, and particularly relates to a diagnostic system that includes an electrophoresis device that rapidly and easily perform blood analysis.

BACKGROUND

Monitoring of the course of diabetes in a patient may be accomplished by checking the glucose level in the blood. However, changes in this level are known to be especially rapid. Glucose assays can give only sporadic information about the patient's blood sugar level, and hence do not reflect the changes in the latter in the weeks preceding the analysis.

Quantitative determination of glycosylated hemoglobin A1 (HbA1c) is known to reflect a patient's average blood glucose concentration over a period of two months preceding the taking of a blood sample. HbA1c is defined by the International Federation of Clinical Chemistry working group (IFCC) as hemoglobin that is irreversibly glycated at one or both N-terminal valines of the beta chains. It is formed from irreversible, slow, non-enzymatic addition of a sugar residue to the hemoglobin, and the rate of production is directly proportional to the ambient glucose concentration. The long lifespan of erythrocytes (mean 120 days) enables HbA1c to be used as an index of glycemic control over the preceding two to three months and as the adequacy of treatment in diabetic patients. For this reason, HbA1c is widely used in a screening test for diabetes mellitus and as a test item for checking whether a diabetic keeps the blood sugar under control.

Conventionally, HbA1c has been measured by HPLC, immunoassay, electrophoresis or the like. HPLC is widely used in clinical examinations. HPLC requires only 1 to 2 minutes to measure each sample, and has achieved a measurement accuracy of about 1.0% in terms of a CV value obtained by a within-run reproducibility test. Measurement methods for checking whether a diabetic keeps the blood sugar under control are required to perform at this level.

Measurement of hemoglobin by electrophoresis has been used for a long time to separate abnormal Hbs with an unusual amino acid sequence. However, separation of HbA1c is significantly difficult, and takes 30 minutes or more by gel electrophoresis. Thus, electrophoresis has been unsatisfactory in terms of measurement time and measurement accuracy when applied to the clinical examinations. Therefore, electrophoresis has hardly been applied to clinical diagnosis of diabetes.

SUMMARY

Embodiments described herein relate to a diagnostic system and electrophoresis device for detecting and/or measuring hemoglobin variants in blood of subject, and particularly relates to a cartridge of an electrophoresis device for a point-of-care diagnostic system for measuring hemoglobin (Hb) types, such as HbA1c, in a subject to determine blood glucose concentration in the subject. In some embodiments, the diagnostic system can be used to measure HbA1c levels to determine glucose levels in a subject having or suspected of having diabetes.

In some embodiments, the cartridge includes a housing having a microchannel structured to receive hemolysate of a blood sample. The microchannel extends between first and second buffer pools each containing about 1 µL to about 200 µL of a buffer solution. The buffer solution exhibits an affinity to non-glycosylated hemoglobin, which facilitates its separation from glycosylated hemoglobin. An electrophoresis strip is positioned within the microchannel and structured to receive at least a portion of the hemolysate. The electrophoresis strip has first and second ends positioned in the first and second buffer pools so as to be at least partially saturated with the buffer solution in each buffer pool. A first electrode is connected to the housing and exposed to the buffer solution in the first buffer pool. A second electrode is connected to the housing and exposed to the buffer solution in the second buffer pool. The first and second electrodes generate an electric field across the electrophoresis strip. A sample loading port extends through the housing to the microchannel and provides access to a portion of the electrophoresis strip configured to receive hemolysate of the blood sample. The application of an electric field to the first and second electrodes induce migration and separation of one or more bands of hemoglobin types in the sample delivered to the electrophoresis strip through the sample loading port. A portion of the housing is optically transparent for visualizing the one or more bands of migrated and separated hemoglobin types on the electrophoresis strip.

In some embodiments, the cartridge includes a first wall, which delimits the first buffer pool, and a second wall, which delimits the second buffer pool. The first and second walls extend the entire width of the microchannel to prevent the buffer solution from flowing out of each buffer pool. At least one first restricting member extends into the first buffer pool and at least one second restricting member extends into the second buffer pool.

In other embodiments, the electrophoresis strip has a length substantially equal to a distance between the at least one first restricting member and the at least one second restricting member such that the first and second restricting members prevent longitudinal movement of the electrophoresis strip relative to the housing. A first electrode connected to the housing is exposed to the buffer solution in the first buffer pool.

In other embodiments, the cartridge includes a cover secured to the housing. The cover includes a projection aligned with the sample loading port and engages the electrophoresis strip when the cover is connected to the housing for preventing movement of the electrophoresis strip during delivery of the blood sample to the electrophoresis strip. The application of an electric field to the first and second electrodes induces migration and separation of hemoglobin in the blood sample delivered to the electrophoresis strip through the sample loading port.

In other embodiments, the diagnostic system includes an electrophoresis band detection module structured to detect through the optically transparent portion of the housing the one or more bands of hemoglobin types on the electrophoresis strip caused by the applied electric field and to generate band detection data based on the one or more bands of migrated and separated hemoglobin types.

In still other embodiments, the diagnostic system includes a processor that receives and analyzes the band detection data to determine one or more band characteristics for each of the one or more bands of hemoglobin types and generate diagnostic results based on the one or more band characteristics.

Other embodiments described herein relate to a diagnostic system for identification and quantification of glycosylated hemoglobin (HbA1c) and non-glycosylated hemoglobin (HbA) in a blood sample. The diagnostic system includes a cartridge, an electrophoresis band detection module, and a processor. The cartridge includes a housing that has a microchannel structured to receive a hemolysate of a blood sample. The microchannel extends between first and second buffer pools each containing about 1 µL to about 200 µL of a buffer solution. The buffer solution exhibits an affinity to non-glycosylated hemoglobin, which facilitates its separation from glycosylated hemoglobin. An electrophoresis strip is positioned within the microchannel and structured to receive at least a portion of a hemolysate. The electrophoresis strip has first and second ends positioned in the first and second buffer pools so as to be at least partially saturated with the buffer solution in each buffer pool. A first electrode is connected to the housing and exposed to the buffer solution in the first buffer pool. A second electrode is connected to the housing and exposed to the buffer solution in the second buffer pool. The first and second electrodes generate an electric field across the electrophoresis strip. A sample loading port extends through the housing to the microchannel and provides access to a portion of the electrophoresis strip configured to receive hemolysate of the blood sample. The application of an electric field to the first and second electrodes induce migration and separation of bands of HbA1c and Hb in the sample delivered to the electrophoresis strip through the sample loading port. A portion of the housing is optically transparent for visualizing the one or more bands of migrated and separated hemoglobin types on the electrophoresis strip.

The electrophoresis band detection module is structured to detect through the optically transparent portion of the housing the HbA1c and HbA bands on the electrophoresis strip caused by the applied electric field and to generate band detection data based on the HbA1c and HbA bands; and The processor receives and analyzes the band detection data to determine one or more band characteristics for each of the HbA1c and HbA bands and generate diagnostic results indicative of HbA1c and HbA quantity in the blood sample. In some embodiments, the processor can be configured to diagnose whether the subject has or is at risk of diabetes.

BRIEF DESCRIPTION OF THE FIGURES

FIG. 6 is another side view of the device of FIG. 1 and an enlarged portion thereof.

FIG. 7 is a schematic illustration of the device of FIG. 1 in use.

FIGS. 11(A-E) illustrate a HemeChip diagnostic system for point-of-care (POC) detection and quantification of hemoglobin variants. (A) Detailed design of HemeChip fabricated using injection molding. (B) HemeChip is compact, single-use, portable, and works on the principles of cellulose acetate electrophoresis. (C) Different Hb types are separated from a stamped blood sample, forming distinct bands on the cellulose acetate strip, based on their net charge in a precisely controlled electrical field in HemeChip. (D) For affinity cellulose acetate electrophoresis, the glycosylated Hb in the stamped sample separates from the non-glycosylated Hb, the non-glycosylated portion has larger mobility due to its affinity to the buffer and thus will travel further towards the anode. (E) The HemeChip system is packaged inside a rugged point of care (POC) device with an embedded GPS designed for use in clinics as well as remote settings.

FIGS. 12(A-B) illustrate identification and quantification of glycosylated hemoglobin (HbA1c) and non-glycosylated hemoglobin (HbA) in blood. Two samples from normal subjects were tested using affinity cellulose acetate electrophoresis. (A) Peak identification and quantification results show 5.2% glycosylated and 94.8% non-glycosylated Hb for subject #875. (B) Peak identification and quantification results show 2.7% glycosylated and 97.3% nonglycosylated Hb for subject #017. (dashed rectangles indicate sample application locations).

DETAILED DESCRIPTION

Figure 1A:
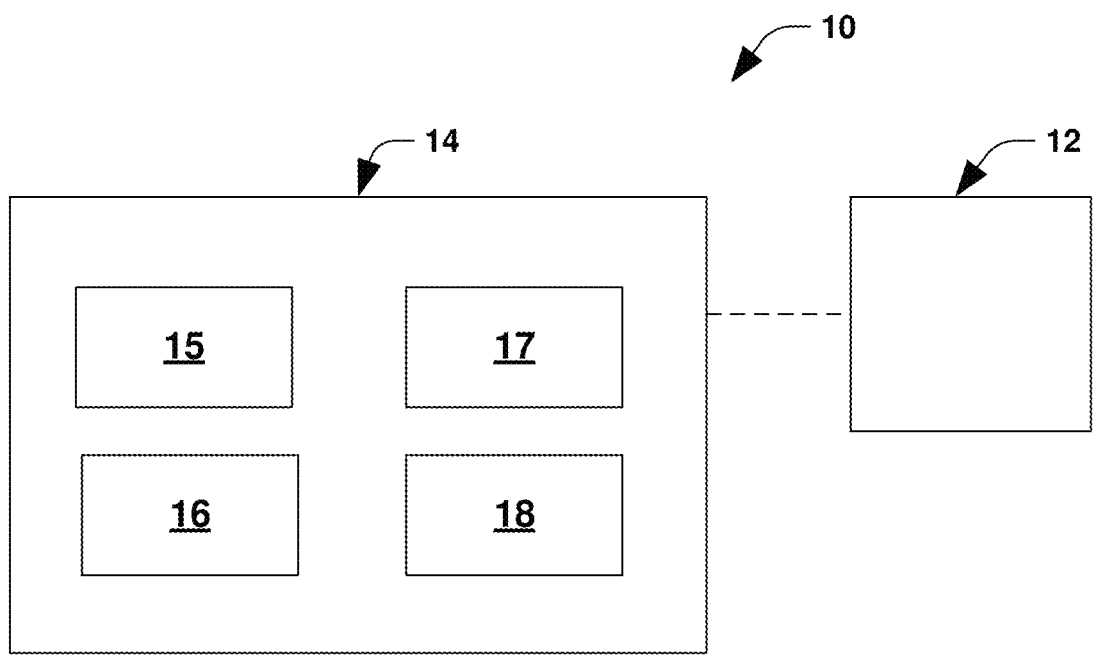
FIGS. 1(A-B) illustrate (A) schematic view of diagnostic system in accordance with an embodiment described herein and (B) an exploded view of an example of a cartridge electrophoresis device.
Figure 1B:
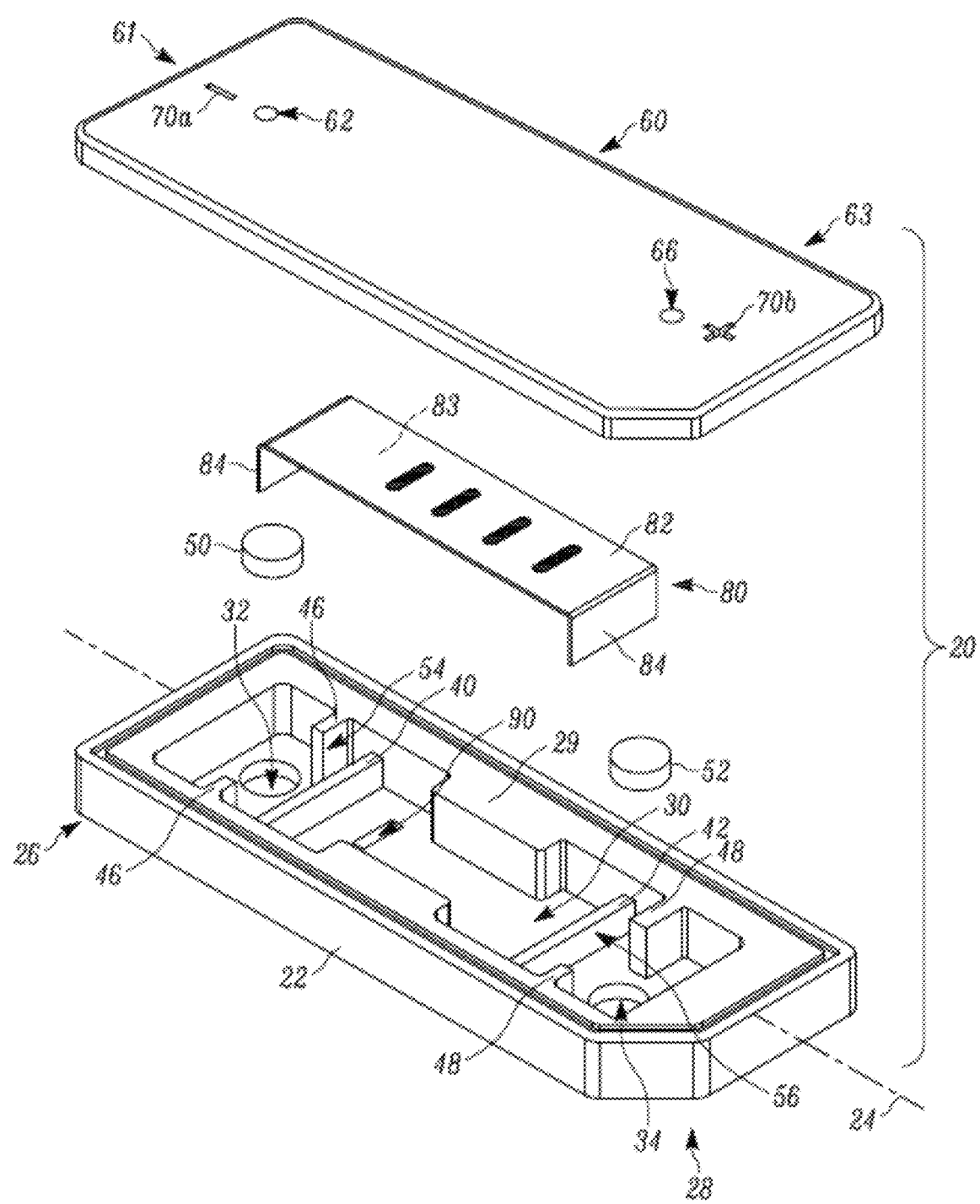
Figure 2:
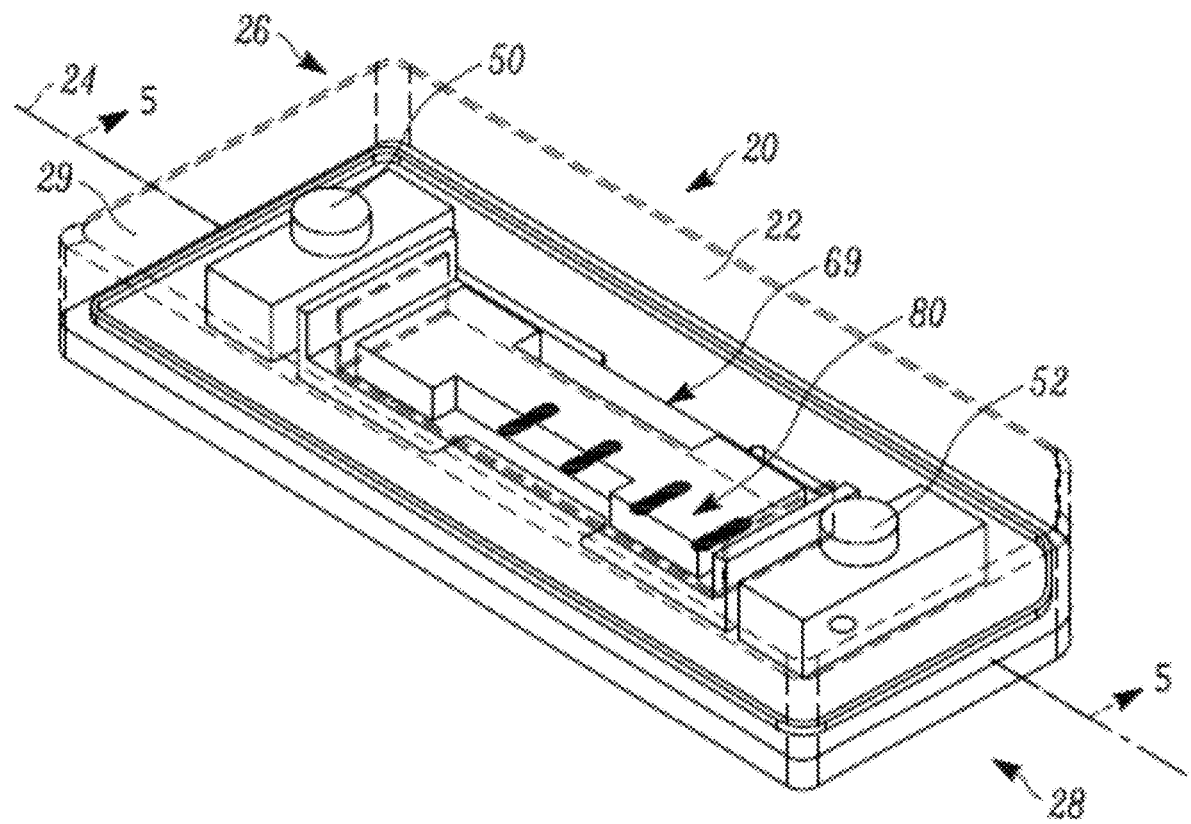
FIG. 2 is a bottom view of the device of FIG. 1.
Figure 3:
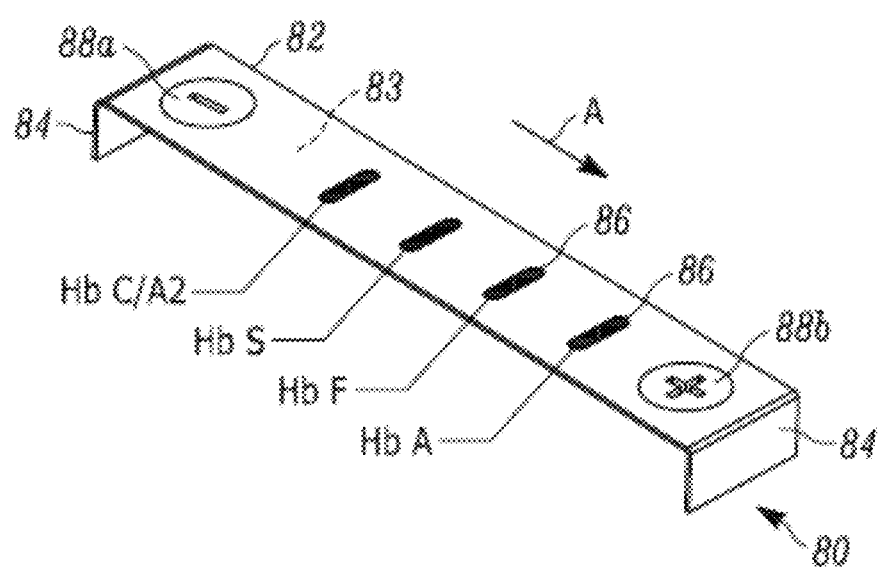
FIG. 3 is a front view of an indicating member of the device of FIG. 1.
Figure 4:
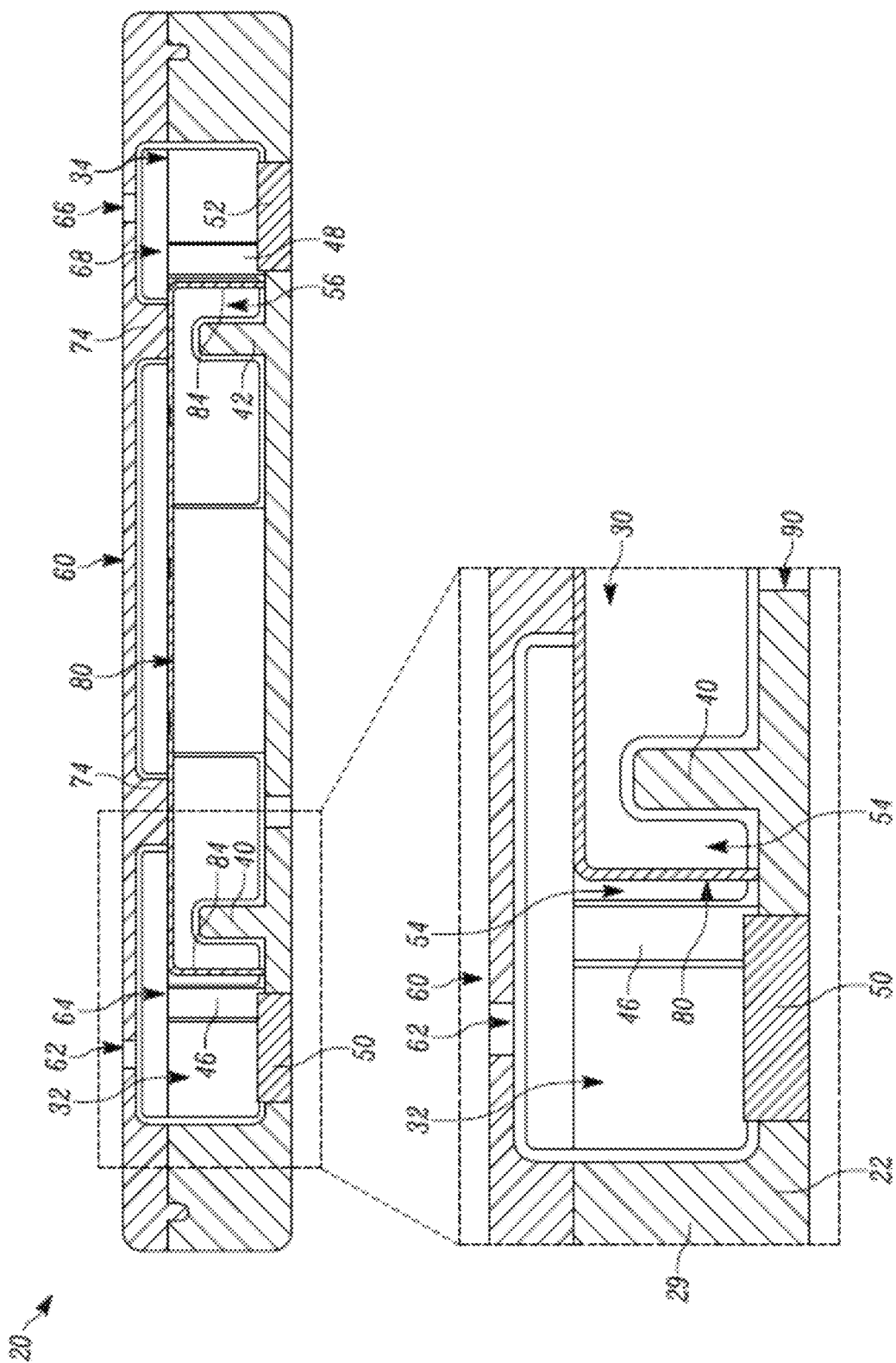
FIG. 4 is a side view of the device of FIG. 1 and an enlarged portion thereof.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "microchannels" as used herein refer to pathways through a medium (e.g., silicon) that allow for movement of liquids and gasses. Microchannels thus can connect other components, i.e., keep components "in liquid communication." While it is not intended that the present invention be limited by precise dimensions of the channels, illustrative ranges for channels are as follows: the channels can be between 0.35 and 100 µm in depth (preferably 50 µm) and between 50 and 1000 µm in width (preferably 400 µm). Channel length can be between 4 mm and 100 mm, or about 27 mm. An "electrophoresis channel" is a channel substantially filled with a material (e.g., cellulose acetate paper) that aids in the differential migration of biological substances (e.g., for example whole cells, proteins, lipids, nucleic acids). In particular, an electrophoresis channel may aid in the differential migration of blood cells based upon mutations in their respective hemoglobin content.

The term "microfabricated", "micromachined" and/or "micromanufactured" as used herein, means to build, construct, assemble or create a device on a small scale (e.g., where components have micron size dimensions) or microscale. In one embodiment, electrophoresis devices are microfabricated ("microfabricated electrophoresis device") in about the millimeter to centimeter size range.

The term "polymer" refers to a substance formed from two or more molecules of the same substance. Examples of a polymer are gels, crosslinked gels and polyacrylamide gels. Polymers may also be linear polymers. In a linear polymer the molecules align predominately in chains parallel or nearly parallel to each other. In a non-linear polymer the parallel alignment of molecules is not required.

The term "electrode" as used herein, refers to an electric conductor through which an electric current enters or leaves.

The term "channel spacer" as used herein, refers to a solid substrate capable of supporting lithographic etching. A channel spacer may comprise one, or more, microchannels and is sealed from the outside environment using dual adhesive films between a top cap and a bottom cap, respectively.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk of" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a compound or sample. In one respect, a compound or sample may be derived from an organism or particular species.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

Embodiments described herein relate to a diagnostic system and electrophoresis device for detecting and/or measuring hemoglobin variants types in blood of subject, and particularly relates to a cartridge for a point-of-care diagnostic system that includes a cartridge electrophoresis device for measuring hemoglobin (Hb) types, such as HbA1c. In some embodiments, the diagnostic system can be used to measure HbA1c levels to determine glucose levels in a subject having or suspected of having diabetes.

FIG. 1A is a schematic illustration of a point-of-care blood diagnostic system 10 in accordance an embodiment described herein. A point-of-care diagnostic system includes devices that are physically located at the site at which patients are tested and sometimes treated to provide quick results and highly effective treatment. Point-of-care devices can provide information and help in diagnosing patient disorders while the patient is present with potentially immediate referral and/or treatment. Unlike gold standard laboratory-based blood testing for disorders, the disclosed point-of-care devices enable diagnosis close to the patient while maintaining high sensitivity and accuracy aiding efficient and effective early treatment of the disorder and/or infection.

The diagnostic system 10 includes a cartridge electrophoresis device 12 for performing electrophoresis analysis on a sample and a reader 14 that can interface with the cartridge 14 to perform electrophoresis, analyze the electrophoresis, and optionally convey and/or display the result to a user of the system 10.

Referring to FIGS. 1B-3, an example cartridge electrophoresis device 20 includes a housing 22, an indicating member 80, and a cover 60. The housing 22 has a generally rectangular shape and extends along a centerline 24 from a first end 26 to a second end 28. A wall 29 of the housing 22 defines a recessed channel 30, i.e., microchannel, which extends between the first and second ends 26, 28. The microchannel 30 can be between about 0.35 and 100 µm in depth (preferably 50 µm) and between about 50 and 1000 µm in width (preferably 400 µm). The microchannel 30 length along the centerline 24 can be between 4 mm and 100 mm (preferably 27 mm).

The microchannel 30 is constructed to receive an electrophoresis strip sieving medium that aids in the differential migration of biological substances, such as whole cells, proteins, lipids, and nucleic acids. More specifically, the electrophoresis strip in the microchannel 30 is configured to suppress convective mixing of the fluid phase through which electrophoresis takes place and contributes to molecular sieving. In one example, the electrophoresis strip can constitute cellulose acetate paper. The electrophoresis channel 30 can aid in the differential migration of hemoglobin variants or types from a hemolysate of blood of a subject.

The wall 29 also helps to define first and second buffer pools 32, 34 located at opposite ends of the channel 30. More specifically, the first buffer pool 32 is positioned at or adjacent to the first end 26 of the housing 22. The second buffer pool 34 is positioned at or adjacent to the second end 28 of the housing.

A first opening 36 extends through the bottom of the housing 22 into the first buffer pool 32. A second opening 38 extends through the bottom of the housing 22 into the second buffer pool 34. As shown, the openings 36, 38 are circular. Alternatively, the openings 36, 38 can have any round or polygonal shape. In any case, an electrode 50 is positioned in the first opening 36 and exposed to the first buffer pool 32. An electrode 52 is positioned in the second opening 38 and exposed to the second buffer pool 34. The electrodes 50, 52 can be made from a conductive material, e.g., steel, 300 stainless steel, graphite and/or carbon.

A wall 40 is positioned within the microchannel 30 and helps define the boundary of the first buffer pool 32. The wall 40 spans the entire width of the microchannel 30 perpendicular to the centerline 24. A pair of restricting members 46 extends from the wall 29 of the housing 22 towards the centerline 24. The restricting members 46 extend parallel to the wall 40 and are positioned closer to the first end 26 than the wall. The restricting members 46 are spaced from one another and spaced from the centerline 24. A gap or space 54 is formed between the restricting members 46 and the wall 40.

A wall 42 is positioned within the microchannel 30 and helps define the boundary of the second buffer pool 34. The wall 42 spans the entire width of the microchannel 30 perpendicular to the centerline 24. A pair of restricting members 48 extends from the wall 29 of the housing 22 towards the centerline 24. The restricting members 48 extend parallel to the wall 42 and are positioned closer to the second end 28 than the wall 42. The restricting members 48 are spaced from one another and spaced from the centerline 24. A gap or space 56 is formed between the restricting members 48 and the wall 42.

An opening 90 extends through the bottom (as shown) of the housing 22 into the microchannel 30 and between the walls 40, 42. The opening 90 can have any shape but regardless is used as a sample loading port by which blood samples can be injected or otherwise supplied to the microchannel 30, as will be described.

The indicating member 80 is elongated and includes a base 82 and a pair of legs 84 extending from the base. The indicating member 80 can be formed from the electrophoresis strip. Optionally, the electrophoresis strip 80 can be secured to or embedded in a hard, conductive material, e.g., metal, as indicated generally in phantom at 83 in FIGS. 1-2. In any case, the indicating member 80 is generally rectangular with the legs 84 extending at an angle, e.g., perpendicular, from the base 82. Consequently, the indicating member 80 can have a U-shaped construction.

A pair of electrode indications 88a, 88b is provided at opposite ends of the base 82. As shown, the indication 88a is a negative (−) terminal indication and the indication 88b is a positive (+) terminal indication. The terminal designations could, however, be reversed.

A series of test indications 86 can be provided along the base 82 between the electrode indications 88a, 88b and parallel to the length of the microchannel 30. Depending on the blood test to be performed, the test indications 86 can be symmetrically or asymmetrically spaced from one another along the base 82. The test indications 86 can be longitudinally aligned with one another or misaligned. The test indications 86 can have the same dimensions or different dimensions from one another. In one example, the test indications 86 are colored bands indicative of the basic types of hemoglobin, e.g., normal hemoglobin ($HbA_0$), fetal hemoglobin (HbF), sickle hemoglobin (HbS), hemoglobin C (HbC or $HbA_2$), and non-glycosylated hemoblobin (HbA), and glycosylated hemoglobin (HbA1c).

The cover 60 is shaped similarly to the housing 22 and extends from a first end 61 to a second end 63. The cover 60 is generally rectangular and configured to be secured to the housing 22. The cover 60 can, for example, form a snap-fit connection with the housing 22. In any case, the cover 60 cooperates with housing 22 to define and enclose the microchannel 30.

A first opening 62 extends through the first end 61 and a second opening 66 extends through the second end 63. A first recess 64 is formed in the underside of the cover 60 and extends to the opening 64. A second recess 68 is formed in the underside of the cover 60 and extends to the opening 66.

The underside of the cover 60 further includes a plurality of support members 74 positioned between the openings 62, 66. As shown, the support members 74 are rectangular projections extending parallel to one another and perpendicular to the length of the cover 22.

A portion 69 of the housing 22 between the ends 26, 28 is transparent or optically clear to define an optical window that allows light to pass into and/or through a portion of the microchannel 30, e.g., the test indications 86 on the indicating member 80 when positioned within the microchannel. The ability to pass light can be a necessary step during analysis of a patient sample within the cartridge 20. The optical window 69 can be a material and/or construction that necessarily or desirably alters light entering the optical window 69 as a part of the analysis of the patient sample within, such as collimating, filtering, and/or polarizing the light that passes through the optical window 69. Alternatively, the optical window 69 can be transparent or translucent, or can be an opening within the housing 22 of the cartridge 20. The cartridge 20 can include a reflector (not shown) opposite the optical window 69 that reflects the incoming light back through the optical window 69 or through another optical window, or can include a further optical window opposite the light entry window to allow light to pass through the cartridge 20.

To this end, the portion or optical window 69 can optionally be provided with a hydrophilic coating to prevent spotting or hazing on the portion 69. The cover 60 and the housing 22 can both be formed from hard, durable materials, such as a plastic, polymer and/or glass.

When the device is assembled, the electrodes 50, 52 are positioned in the openings 36, 38 and extend into each buffer pool 32, 34. The legs 84 of the indicating member 80 are inserted into the gaps 54, 56 at each end 26, 28 of the housing 22 such that the indicating member 80 extends parallel to/along the housing centerline 24 within or adjacent to the microchannel 30. The restricting members 46, 48 and walls 40, 42 are longitudinally spaced from one another in a manner that prevents or limits longitudinal movement of the indicating member 80 relative to the housing 22. More specifically, the indicating member 80—in particular the electrophoresis strip, e.g., cellulose acetate paper—has a length substantially equal to the longitudinal distance between the restricting members 46, 48 such that the indicating member abuts the restricting members to prevent relative longitudinal movement therebetween.

The first buffer pool 32 and the second buffer pool 34 each receive a buffer solution 51, 53 that at least partially saturates the indicating member 80 extending into the respective pool. The buffer solution 51, 53 can exhibit an affinity to non-glycosylated hemoglobin, facilitate its separation from glycosylated hemoglobin, and thus be used for HbA1C testing.

In some embodiments, the buffer solution can be mildly acidic, for example, a pH of about 4.5 to about 6.7, (e.g., pH 6.4), and include a sulfated polysaccharide. The sulfated polysaccharide can bind to or exhibit an affinity to non-glycosylated hemoglobin. The sulfated polysaccharide is not particularly limited, and a known sulfated polysaccharide can be used. Specific examples include compounds for introducing a sulfate group to a neutral polysaccharide, such as cellulose, dextran, agarose, mannan or starch, or a derivative thereof, and salts of thereof; chondroitin sulfate; dextran sulfate; heparin; heparan; fucoidan; and the like. In certain embodiments, the sulfated polysaccharide can include dextran sulfate.

The buffer solution can also include organic acids such as citric acid, succinic acid, tartaric acid, and malic acid and salts thereof; amino acids such as glycine, taurine and arginine; inorganic acids, such as hydrochloric acid, nitric acid, sulfuric acid, phosphoric acid, boric acid and acetic acid, and salts thereof; and the like. Optionally, a generally used additive may be added to the above-mentioned buffer solution. Examples thereof include surfactants, various polymers, hydrophilic low-molecular-weight compounds, and the like.

By way of example, the buffer solution can include 33 mmol citrate, 2 μmol dextran sulfate, and 8 μmol disodium EDTA per liter, at a pH of 6.4. The buffer pools 32, 34 can each receive about 1 μL to about 200 μL of the respective buffer solution 51, 53.

The cover 60 is secured to the housing 22 to confine the indicator member 80 within the microchannel 30. The opening 62 in the cover 60 is aligned with the electrode 50 within the first buffer pool 32. The negative electrode indication 88a is generally positioned between the opening 62 and the electrode 50. The opening 66 in the cover 60 is aligned with the electrode 52 within the second buffer pool 34. The negative electrode indication 88b is generally positioned between the opening 66 and the electrode 52.

When the cover 60 is secured to the housing 22 the optical window 69 of the housing is aligned with the indicating member 80 such that all the test indications 86 on the electrophoresis strip are visible through the optical window 69. In other words, the support members 74 on the cover 60 do not visually obstruct the test indications 86 through the optical window 69.

Figure 5:
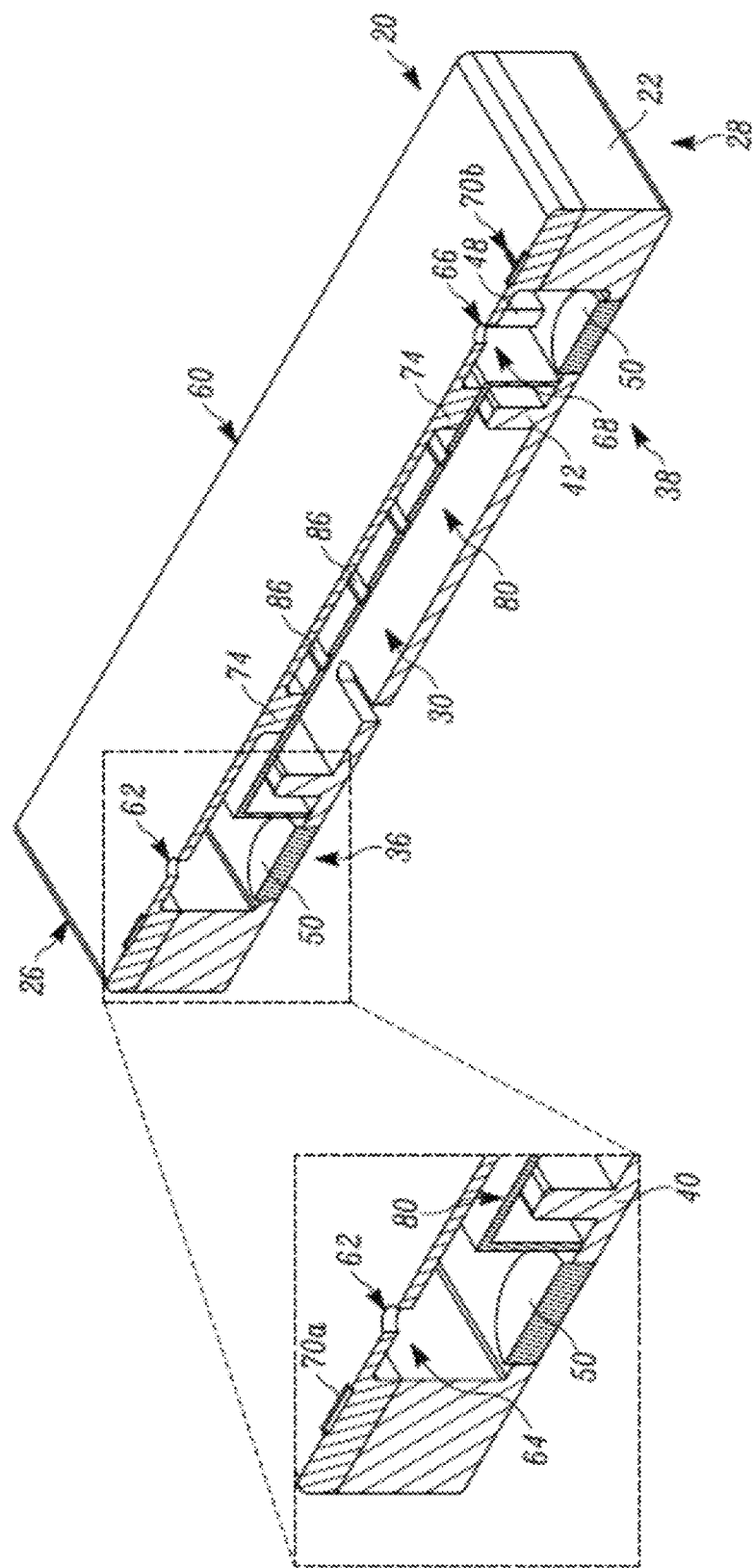
FIG. 5 is a section view of the device of FIG. 2 taken along line 5-5.

Referring to FIG. 5, an electrode 94 is inserted through the opening 62 in the cover, into the first buffer pool 32, and into contact with the electrode 50. An electrode 96 is inserted through the opening 66 in the cover, into the second buffer pool 34, and into contact with the electrode 52. The electrodes 94, 96 are electrically connected to a power supply 98. The electrodes 50, 52, 94, 96, buffer solutions 51, 53 and indicating member 80 cooperate to form an electrical circuit through the cartridge electrophoresis device 20.

The power supply 98 is capable of generating an electric field of about 1V to about 400V. In some instances, the voltage applied to the cartridge electrophoresis device 20 by the electrodes 94, 96 does not exceed 250V. Regardless, an electric field is generated across the electrophoresis strip of the indicating member 80 effective to promote migration of hemoglobin variants in a blood sample along the electrophoresis strip.

A patient sample, such as patient blood sample, can be provided in the cartridge 20 and on the electrophoresis strip using a sample applicator 92. The sample applicator 92 provides a more precise and/or controlled deposition of the sample onto the electrophoresis strip. Additionally, the patient sample can include added compounds/components, such as one or more markers. The added compounds/components can assist with the electrophoresis process and/or assist with interpreting the electrophoresis results.

For example, the one or more markers can have known migrations rates and/or distances for a given applied voltage and/or voltage application time. Alternatively, these markers can normalize the results of the electrophoresis process by having migration rates relative to the sample, thereby reducing the effects of sample-to-sample variability. These markers can assist with evaluating the resultant banding of the patient sample.

A sample applicator 92 is filled with hemolysate of a blood sample BS and inserted into the loading port 90 on the underside of the housing 22. The hemolysate of the blood sample BS introduced into the loading port 90 can be, for example, less than about 10 μL. The cartridge electrophoresis device 20 can therefore be microengineered and capable of processing a small volume, e.g., a finger or heel prick volume.

In any case, the sample applicator 92 is urged in the direction D towards the indicating member 80. The loading port 90 therefore helps to guide the sample applicator 92 towards a desired location on the indicating member 80. Since the indicating member 80 is formed from the electrophoresis strip, the sample applicator 92 can be inserted to the strip and release the sample BS therein to the left [as shown in FIG. 6] of all the test indications 86.

The loading port 90 is aligned with and extends towards one of the support structures 74. As a result, the support members 74—especially the leftmost support member—acts as a reaction surface to the indicating member 80 as the sample applicator 92 extends into the electrophoresis strip and deposits the sample therein. The support member 74 thereby prevents movement of the indicating member 80 away from the moving sample applicator 92. This helps prevent deformation or distortion of the indicating member 80 and helps the user release the sample in the proper location along the indicating member.

Once the sample BS is released in position, the sample applicator 92 is withdrawn (in a direction opposite D) from the electrophoresis device 20. Capillary action by the electrophoresis strip 80 can maintain the sample BS in position. The power supply 98 is actuated/turned on, which supplies current to the buffer pools 32, 34 and indicating member 80 as described, which establishes a continuous electrical path through the device 20 via the buffer pools 32, 34 and cellulose acetate paper 80 in contact therewith.

In this example, forming the indicating member 80 out of cellulose acetate paper allows the indicating member to also act as the sieving medium during the electrophoresis process. To this end, hemoglobin in the hemolysate of the blood sample BS are moved through the indicating member 80 and towards the positive electrode 52 in the direction indicated by A (FIG. 7).

With the patient sample in place, a voltage is applied using the electrodes, causing hemoglobin variant types to migrate across the electrophoresis strip over a defined time. The various hemoglobin types will separate into bands due to the applied voltage and the physical and electrical properties of the various hemoblobin types. One or all of the applied voltage, current and the application time can be predetermined or preset based on the various parameters of the electrophoresis testing being performed. Alternatively, one or more of the voltage, current and application times can be variable and based on the banding of the patient sample or an added compound/component therein. For example, the movement of a marker added to the patient sample can be monitored as the marker moves across the electrophoresis strip. That is, imaging/monitoring of the electrophoresis testing, and/or the markers thereon, can be performed in a continuous or timed interval manner during the testing process. For example, images of the electrophoresis process can be continuously captured, such as by a video imaging process, or the images can be captured at regular intervals based on time and/or the distance one or more bands have traveled. Once the marker has reached a predetermined location across the electrophoresis strip, the test can be terminated with the removal of the applied voltage.

After a predetermined time, the power supply 98 is turned off and the hemoglobin variants are frozen in their respective positions along the length of the indicating member 80 and relative to the various test indications 86. Depending on the distribution of the hemoglobin 86 a diagnosis regarding the sample BS can be made. To this end, the transparent portion 69 of the housing 22 allows the reader to simply visualize the distribution of hemoglobin relative to the test indications 86 on the indicating member 80. Consequently, a diagnosis regarding the sample BS can quickly be made. In the example shown, the user can identify different hemoglobin distributions within the hemolysate of the blood sample BS and readily diagnose any deficiencies or hemoglobin-related conditions.

The configuration of the cartridge electrophoresis device 20 is advantageous for several reasons. First, as noted, the support structures 74 provided on the cover 60 help prevent movement of the indicating member 80 while the sample BS is injected/provided into the cellulose acetate paper forming the indicating member. Second, the walls 40, 42 and associated restricting members 46, 48 each help prevent or limit relative movement between the indicating member 80 and the housing 22 during loading and operation of the device 20.

Moreover, the wall 40 also helps to prevent the buffer solution 51 within the first buffer pool 32 from leaking into the microchannel 30 via capillary action. Similarly, the wall 42 helps to prevent the buffer solution 53 within the second buffer pool 34 from leaking into the microchannel 30 via capillary action. The walls 40, 42 help ensure current flow through the device 20 is continuous and helps the device maintain a substantially constant pH during operation.

Additionally, embedding the electrodes 50, 52 within the bottom of the buffer pools 32, 34 helps to ensure a consistent supply of electric field through the cellulose acetate paper on the indicating member 80, even when/if either buffer solution 51, 53 begins to evaporate.

The reader 14 can include a housing (not shown) that surrounds and encloses some portion or all of the reader components. The housing of the reader 14 is constructed of materials, which may involve a suitably robust construction such that the reader 14 is rugged and portable. Alternatively, the reader 14 can be designed and/or constructed for use in a permanent or semi-permanent location, such as in a clinic or laboratory.

The housing of the reader 14 includes a cartridge interface that interacts with and/or engages the cartridge 12 for analysis of a patient sample. The cartridge interface can be a slot that is shaped to receive the cartridge 12. Alternative designs and/or structures of cartridge interfaces can be used with the reader 14.

The reader 14 can include an electrophoresis module 15 that can interface with the cartridge 12 to perform the electrophoresis test. The electrophoresis module 15, alone or in conjunction with processing circuitry, can control the electrophoresis test, including voltage/current application time and/or level. The electrophoresis module can supply electrical power from the power supply 98 to the cartridge 12, or electrophoresis strip, directly, to establish the necessary voltage across the electrophoresis strip for testing. The voltage can be applied at a higher level to increase the speed of the testing, however, the increased speed can cause decreased band fidelity, which can increase the difficulty and error of the band analysis and evaluation. A lower applied voltage can increase band fidelity but can lengthen the required testing time. Alternatively, the electrophoresis module 15 can vary the applied voltage or current, while maintaining the other stable, to achieve a desired or required level of band fidelity and testing speed. For example, an initial test to identify a patient condition can be carried out at a higher level voltage level to speed the test and a subsequent test to quantify the condition can be carried out a lower voltage level to generate clearer or more accurate results.

An electrophoresis band detection module 16, alone or in conjunction with the electrophoresis module 15, can capture, analyze and/or evaluate the electrophoresis test results and/or any other band detection characteristic(s) related to or otherwise based on the electrophoresis test results. The electrophoresis band detection module 16 can include an imaging device, such as a digital image sensor, to capture an image of the electrophoresis strip and the banding thereon at the conclusion of the electrophoresis test. Using the captured image data, each of the bands can be associated with one or more compounds/components of the patient blood sample and the proportions of each can be determined.

The reader 14 can also include an output 17 that includes one or more visual and/or audible outputs although in other examples the output is data and does not include visual and/or audible outputs. The output 17 communicates information regarding the status of the reader 14, the results of analysis of a patient sample, instructions regarding use of the reader 14 and/or other information to a user or other computing device. The output 17 can include a display, such as a screen, such as a touchscreen, lights, and/or other visual indicators. The touchscreen used to display information, such as analysis results, to the user can also be used by a user to input to the reader 14. Alternative interfaces can be included on and/or connected to the reader 14, such as a keyboard and/or mouse. Additionally, user devices, such as a cellphone or tablet, can be connected to the reader 14 to provide an interface portal through which a user can interact with the reader 14. The audible output 17 can include a speaker, buzzer, or other audible indicators. The output 17 can be output through an external device, such as a computer, speaker, or mobile device connected physically and/or wirelessly to the reader 14. The output 17 can output data, including the collected analysis data and/or interpretative data indicative of the presence or absence of a disorder, condition, infection and/or disease within the patient and/or the patient sample. An example can include the identification and proportions of the various hemoglobin types within the patient sample. The interpretive data output can be based on the analysis data collected and processed by the processing circuitry of the reader 14.

The reader can further include a sample processing module 18. The sample processing module 18 can receive inputs from the electrophoresis band detection module 16. Based on the received band detection data the sample processing module 16 can determine at least a characteristic of the patient sample, such as a disease or condition, an identity of the various compounds/components of the patient sample and quantification of the various compounds/components of the patient sample. The sample processing module 18 can output the identification and proportions of the compounds/components, and/or other various data based on the analysis of the patient sample. For example, the sample processing module 18, using the band detection data from the electrophoresis band detection module 16, can identify and quantify the various hemoglobin types of the patient sample. The output from the sample processing module 18 can be transmitted through the output 17 of the reader 14 or transmitted to an external device and/or system, such as a computer, mobile device, and remote server or database.

The sample processing module 18 can analyze the patient sample to determine a hemoglobin characteristic, such as a hemoglobin affecting disease and/or condition, based on the data from various components, elements and/or systems of the reader 14. The results of the analysis can be output from the sample processing module 18 to the output 17 to convey the information to a user or other.

Figure 9A:
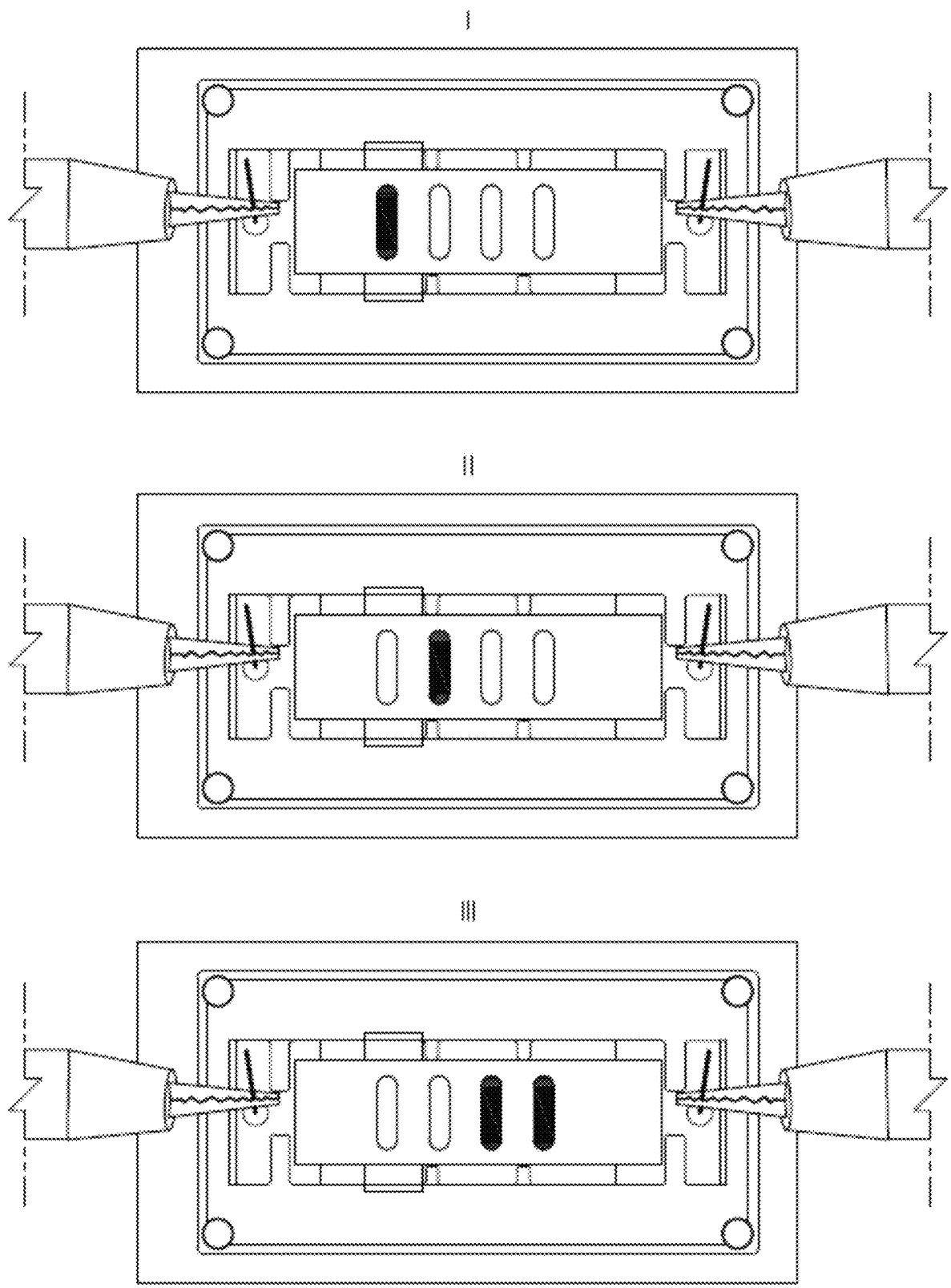
FIGS. 9A-9B illustrate images showing time lapse photos and schematic illustrations of a electrophoresis test.
Figure 9B:
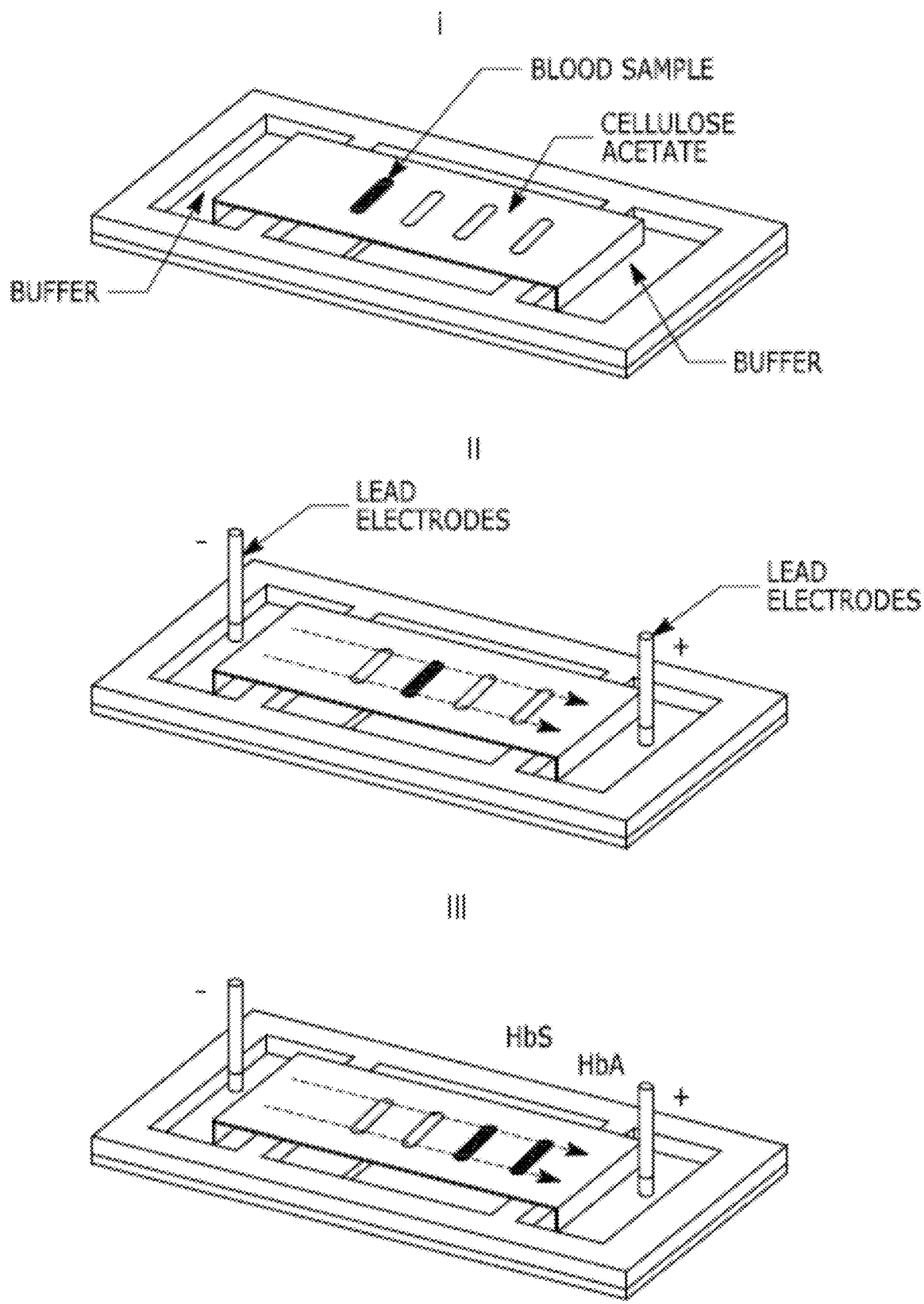

Referring to FIGS. 9(A-B), another example of a cartridge electrophoresis device or 200 can include a housing having first and second buffer ports, a sample loading port, and first and second electrodes. The housing also includes a microchannel that extends from a first end to a second end of the housing. The microchannel contains an electrophoresis strip (e.g., cellulose acetate paper) that is at least partially saturated with a buffer solution that exhibits an affinity to non-glycosylated hemoglobin, which facilitates its separation from glycosylated hemoglobin, and can thus be used for HbA1C testing. The first buffer port and the second buffer extend, respectively, through the first end and second of the housing to the microchannel and electrophoresis strip. The first buffer port and the second buffer port are capable of receiving the buffer solution that at least partially saturates the electrophoresis strip.

The sample loading port can receive hemolysate of a blood sample and extends through the first end of the housing to the microchannel and cellulose acetate paper. The first electrode and the second electrode can generate an electric field across the electrophoresis effective to promote migration of hemoglobin variants in the hemolysate of the blood sample along the cellulose acetate paper. The first electrode and second electrode can extend, respectively, through the first buffer port and the second port to the electrophoresis strip.

In some embodiments, the housing can include a top cap, a bottom cap, and a channel spacer interposed between the top cap and the bottom cap. The channel spacer can define the channel in the housing. The top cap, bottom cap, and channel spacer can be formed from at least one of glass or plastic.

In some embodiments, the diagnostic system can further include a reader that includes an imaging system for visualizing and quantifying hemoglobin variant band migration along the electrophoresis strip for blood samples introduced into the sample loading port. The housing can include a viewing area for visualizing the cellulose acetate paper and hemoglobin variant migration.

The first electrode and the second electrode can be connected to a power supply. The power supply can generate an electric field of about 1V to about 400V. In some embodiments, the voltage applied to the cartridge by the electrodes does not exceed 250V.

The cartridge can be microengineered and be capable of processing a small volume (e.g., for example, a fingerprick volume or a heelprick volume).

The sample can be a blood sample that can be optionally treated, if necessary or desired, for analysis. The treatment of the blood sample can include diluting the blood sample, which can be done by mixing the collected blood sample with a dilutant, such as deionized water or other fluid that dilutes the blood sample. The dilutant can alter the viscosity of the blood sample, the opacity or translucence of the blood sample, or otherwise prepare the blood sample for analysis using the reader. Preferably, the dilutant does not impact the resulting analysis of the blood sample and/or assists with preparing the blood sample for analysis. This can include lysing the cells of the blood sample to release the various cellular components for electrophoresis analysis by the reader. Lysing agents can include fluids, such as water or various chemicals, and powders. Additionally, mechanical lysing can be used, such as by sonication, maceration and/or filtering, to achieve adequate lysing of the cells of the blood sample in preparation for analysis of the sample.

One or more markers can be added to the blood sample. The added markers can assist with visualizing the completed electrophoresis results. For example, a marker that moves at the same relative rate as a hemoglobin type due at a predetermined applied voltage can be added. The marker will move with the hemoglobin type containing portion of the blood sample across the electrophoresis strip in response to the applied voltage. The marker can have a color, or other optical properties that makes visualizing the marker easier. Since the marker moves with the relative to a specific hemoglobin type, the easier to visualize marker can make it easier to determine the distance the hemoglobin type has moved across the electrophoresis strip in response to the applied voltage.

In other embodiments, the sample introduced into the sample loading port can be less than 10 μL. The buffer solution can include alkaline tris/Borate/EDTA buffer solution. The first electrode and the second electrode can include graphite or carbon electrodes.

In other embodiments, the imaging system can include a mobile phone imaging system to visualize and quantify hemoglobin variant migration. For example, as shown in FIG. 10, the mobile phone imaging system can include a mobile telephone that is used to image hemoglobin variant migration and a software application that recognizes and quantifies the hemoglobin band types and thicknesses to make a diagnostic decision. The hemoglobin band types can include hemoglobin types C/A, S, F, A0, A1, and A1c.

In some embodiments, the diagnostic system can be used to diagnose whether the subject has hemoglobin variants HbAA, HbSS, HbSA, HbSC, HbA2, HbA1, and HbA1c. In other embodiments, the diagnostic system can be used to diagnose whether the subject has or an increased risk of diabetes.

In some embodiments, the diagnostic system can be used in a method where hemolysate of a blood sample from a subject is introduced into the sample loading port. The blood sample includes hemoglobin. Hemoglobin bands formed on the cellulose acetate paper are then imaged with the imaging system to determine hemoglobin phenotype for the subject.

The hemoglobin phenotype can selected from the group consisting of HbAA, HbSA, HbSS, HbSC, HbA2, HbA1, and HbA1c.

In some embodiments, the cartridge comprises biomedical grade poly methyl methacrylate (PMMA, McMaster-Carr) substrates and a double sided adhesive film (DSA) (3M Company), which have been shown to be biocompatible and non-cytotoxic in biomedical and clinical applications. Cartridges may be fabricated using a micromachining platform (e.g., X-660 Laser, Universal Laser Systems) to create a variety of structures including, but not limited to, inlet ports, outlet ports, sample ports, microfluidic channels, reaction chambers, and/or electrophoresis channels. (FIG. 8A) Microfluidic channel dimensions may be controlled to within 10 µm. In other embodiments, the diagnostic system allows rapid manual assembly and is disposable (e.g., for example, a single use cartridge) to prevent potential cross-contamination between patients.

One advantage of the diagnostic system described herein, and particularly, the cartridge electrophoresis device, is that it is suitable for mass-production which provides efficiency in point-of-care technologies. The diagnostic system can provide a low cost screen test for monitoring glucose levels and diabetes in a subject. It is mobile and easy-to-use; it can be performed by anyone after a short (30 minute) training. The diagnostic system described herein can integrate with a mobile device (e.g., IPhone, IPod) to produce objective and quantitative results. If necessary, cartridge electrophoresis devices and/or their components may be sterilized (e.g., by UV light) and assembled in sterile laminar flow hood. Sterile biomedical grade silicon tubing (Tygon Biopharm Plus) may be integrated to the cartridge electrophoresis devices and cartridge electrophoresis devices may be sealed to prevent any leakage. Further, tubing allows simple connection to other platforms, such as in vitro culture systems for additional analyses if needed.

In other embodiments, a mobile imaging and quantification algorithm can be integrated into the diagnostic system and/or reader. The algorithm can achieve reliable and repeatable test results for data collected in all resource settings of the diagnostic system.

Figure 10A:
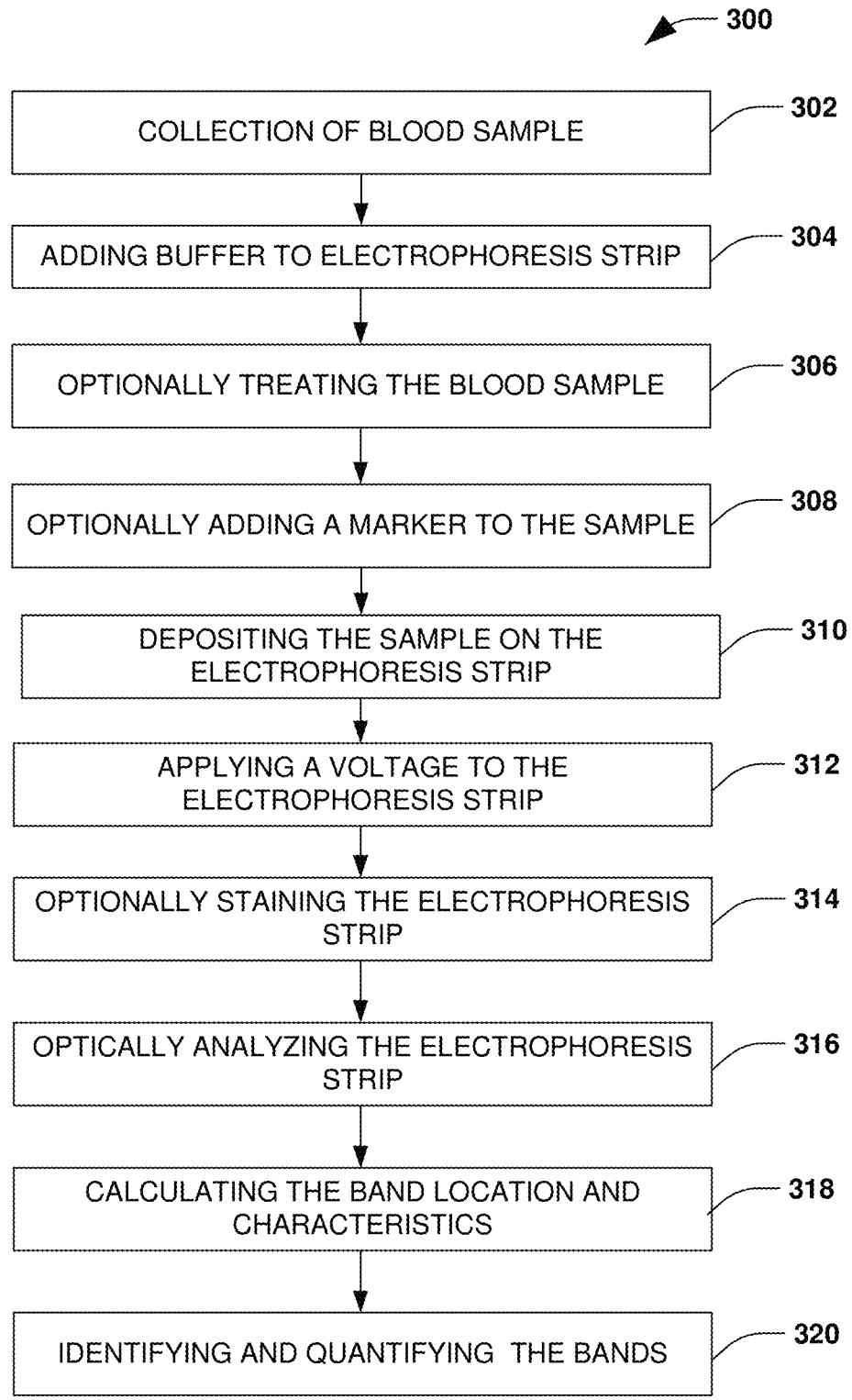
FIGS. 10(A-B) illustrate schema showing (A) a method of using the diagnostic system described herein; and (B) a web-based image processing data flow and results comparison.

FIG. 10A is an example analysis method 300 identifying and quantifying glycosylated hemoglobin (HbA1c) and non-glycosylated hemoglobin (Hba). The analysis of a patient sample, which is patient blood in this example, is performed to determine average blood glucose concentration over a period of two months preceding the taking of a blood sample. The example method of FIG. 10A can be performed using a reader and cartridge, such as the example shown in FIG. 1. The reader can include one or more systems and/or elements to analyze, quantify, identify and/or otherwise determine HbA1c characteristics of a patient sample that can be indicative of the presence of diabetes in the patient.

An initial step 302 of the method 300 can include the collection of a patient sample for analysis, in this example, a blood sample.

At 304, a buffer can be added to the electrophoresis strip in preparation for the electrophoresis testing of the collected blood sample. The buffer solution can exhibit an affinity to non-glycosylated hemoglobin, facilitate its separation from glycosylated hemoglobin, and thus be used for HbA1C testing.

In some embodiments, the buffer solution can be mildly acidic, for example, a pH of about 4.5 to about 6.7, (e.g., pH 6.4) and include a sulfated polysaccharide. The sulfated polysaccharide can bind to or exhibit an affinity to non-glycosylated hemoglobin. The sulfated polysaccharide is not particularly limited, and a known sulfated polysaccharide can be used. Specific examples include compounds for introducing a sulfate group to a neutral polysaccharide, such as cellulose, dextran, agarose, mannan or starch, or a derivative thereof, and salts of thereof; chondroitin sulfate; dextran sulfate; heparin; heparan; fucoidan; and the like. In certain embodiments, the sulfated polysaccharide can include dextran sulfate.

The buffer solution can also include organic acids such as citric acid, succinic acid, tartaric acid, and malic acid and salts thereof; amino acids such as glycine, taurine and arginine; inorganic acids, such as hydrochloric acid, nitric acid, sulfuric acid, phosphoric acid, boric acid and acetic acid, and salts thereof; and the like. Optionally, a generally used additive may be added to the above-mentioned buffer solution. Examples thereof include surfactants, various polymers, hydrophilic low-molecular-weight compounds, and the like.

By way of example, the buffer solution can include 33 mmol citrate, 2 µmol dextran sulfate, and 8 µmol disodium EDTA per liter, at a pH of 6.4.

The collected blood sample 302 can then be treated at step 306, if necessary or desired, for analysis. The treatment of the blood sample can include diluting the blood sample, which can be done by mixing the collected blood sample with a dilutant, such as deionized water or other fluid that dilutes the blood sample. The dilutant can alter the viscosity of the blood sample, the opacity or translucence of the blood sample, or otherwise prepare the blood sample for analysis using the reader. Preferably, the dilutant does not impact the resulting analysis of the blood sample and/or assists with preparing the blood sample for analysis. This can include lysing the cells of the blood sample to release the various cellular components for electrophoresis analysis by the reader. Lysing agents can include fluids, such as water or various chemicals, and powders. Additionally, mechanical lysing can be used, such as by sonication, maceration and/or filtering, to achieve adequate lysing of the cells of the blood sample in preparation for analysis of the sample.

At 308, one or more markers can be optionally added to the blood sample. The added markers can assist with visualizing the completed electrophoresis results. For example, a marker that moves at the same relative rate as a hemoglobin type due at a predetermined applied voltage can be added. The marker will move with the hemoglobin type containing portion of the blood sample across the electrophoresis strip in response to the applied voltage. The marker can have a color, or other optical properties that makes visualizing the marker easier. Since the marker moves with the relative to a specific hemoglobin type, the easier to visualize marker can make it easier to determine the distance the hemoglobin type has moved across the electrophoresis strip in response to the applied voltage.

At 310 the blood sample can be deposited onto the electrophoresis strip in a controlled manner, preferably applied in a "line" perpendicular to the length of the electrophoresis strip. The controlled manner of deposition can include controlling the amount of blood sample deposited, the area across which the blood sample is deposited, the shape of the area across which the blood sample is deposited and/or other deposition characteristics. One or more systems and/or components of the reader and/or cartridge can be used to deposit the blood sample in the controlled manner onto the electrophoresis strip.

With the blood sample deposited onto the electrophoresis strip, a voltage can be applied across the electrophoresis strip at 312 to cause the separation of the blood sample into various bands of glycosylated hemoglobin and non-glycosylated hemoglobin. The voltage or current can be applied at a predetermined level or series of levels and for an amount of time. As discussed previously, the application time of the voltage can be predetermined or based on the movement of one or more bands of the patient sample, measurement of an electrical parameter such as resistance or an added compound/component. A higher applied voltage can cause the bands to move across the electrophoresis strip at a greater speed, however, the band shape can be distorted making the interpretation of the banding difficult. A lower applied voltage can increase band fidelity but can take a longer time to perform the requisite testing. The applied voltage can be selected to optimize testing efficiency while maintaining a desired or minimum fidelity level. Further, the applied voltage can be varied during testing, such as applying a higher voltage initially and then applying a lower voltage. The varied application of the voltage can cause the initial band separation and movement and the later applied lower voltage can assist with increasing the fidelity of the resultant banding pattern. Additionally, varying voltages and/or currents can be applied during the electrophoresis process in response to a measurement of the bands formed by the blood and/or the band or bands formed by the markers in a predetermined ratio, to maintain a constant rate of travel of the marker band or a portion thereof.

After completion of the electrophoresis process, the electrophoresis strip can be optionally stained at 314. Staining the electrophoresis strip and the bands thereon can assist with the analysis and/or evaluation of the banding. For example, a stain for hemoglobin can be used to stain the bands to assist with determining a position of the bands across the electrophoresis strip. The cartridge and/or reader can include the stain and the required systems/components for applying the stain to the electrophoresis strip. Alternatively, a user can stain the electrophoresis strip before band analysis. Alternatively or in addition, a short high voltage can be applied at the end of the test essentially burning the hemoglobin bands and making them visually persistent. The high voltage may also reduce the risk of viable pathogens.

At 316, the electrophoresis strip can be optically analyzed, including imaging the electrophoresis strip and the bands thereon. The electrophoresis strip can be imaged using one or more light sources emitting one or more spectrums of light. Multiple images of the electrophoresis strip can be captured in various lighting conditions in order to assist with analyzing/evaluating the bands. The image capture can be accomplished using one or more imaging sensors, such as a digital imaging sensor and can be performed throughout the testing process or at the conclusion of the test. The captured image(s) can be processed to evaluate and/or analyze the electrophoresis test results.

At 318, the final location and characteristics of the bands can be calculated. The calculation can determine the distance each of the bands traveled, due to the applied voltage during testing, from the initial blood sample placement on the electrophoresis strip as well as the area of the bands. Along with the distance of travel, a speed of travel of each band can be calculated based on the elapsed voltage application time and the distance traveled. Using the identity, area, and location of each of the bands, the various components/compounds of the initial blood sample, and their proportions, can be determined.

As part of the analysis of the electrophoresis tests, the bands formed during the testing can be identified and quantified at 320. Identification of the bands can include associating one or more compounds/components of the initial blood sample with each of the bands of the electrophoresis. For example, identifying the bands can include associating each of the bands with a hemoglobin type. The identification of the bands can be assisted by markers that were previously added to the blood sample prior to the electrophoresis testing. The markers can be selected so that their final position along the electrophoresis test aligns with one or more of the compounds/components of interest in the blood sample. Alternatively, the marker can be selected to be interspersed between two bands so assist with differentiating the bands for identification.

Once the analysis of the blood sample is complete, the results can be output. The output of the results can include the identified and quantified HbA1c relative to non-glycosylated hemoglobin, which can be indicative of diabetes. The output can be displayed or relayed to the user in a visual output, such as on a display, auditory such as by a speaker, or other manner. This can include transmitting the output results to an external device, such as a computer, through a wired or wireless connection or communication protocol, such as by a Bluetooth connection.

Figure 10B:
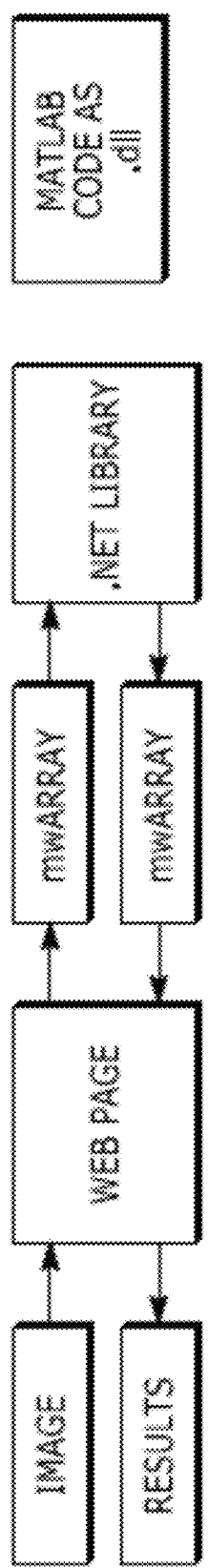

Referring to FIG. 10B, in some embodiments, imaging of the electrophoresis cartridge and data analysis may be performed using a reader that includes mobile or portable computer interfacable imaging system or application to enhance reliability and reproducibility of blood analyses. The imaging system can include a CMOS camera used to image, for example, hemoglobin variant migration and a software application that recognizes and quantifies the hemoglobin band types and thicknesses to make a screening decision.

To this end, an image processing algorithm can initially recognize a microfluidic channel by using exemplary sample ports as position markers. Then, red (R) pixel values may be extracted from a color image and normalized with respect to background. Red pixel intensity histograms may be plotted automatically along the channel, thereby determining the positions of highest intensity (FIG. 10B)

The application segments, counts, and quantifies the bands that correspond to different Hb types, and hence different Hb disorders on electrophoresis strip. For example, Hb1A and/or Hb1Ac positions can be determined for each sample using histogram plots, and the results displayed on a screen. Graphical user interface includes essential features, including fiducial markers for self-calibration that guide the user to properly align the camera field-of-view. The application can input date, location, and a unique patient identifier.

Example

Materials and Methods
HemeChip Materials

Figure 8A:
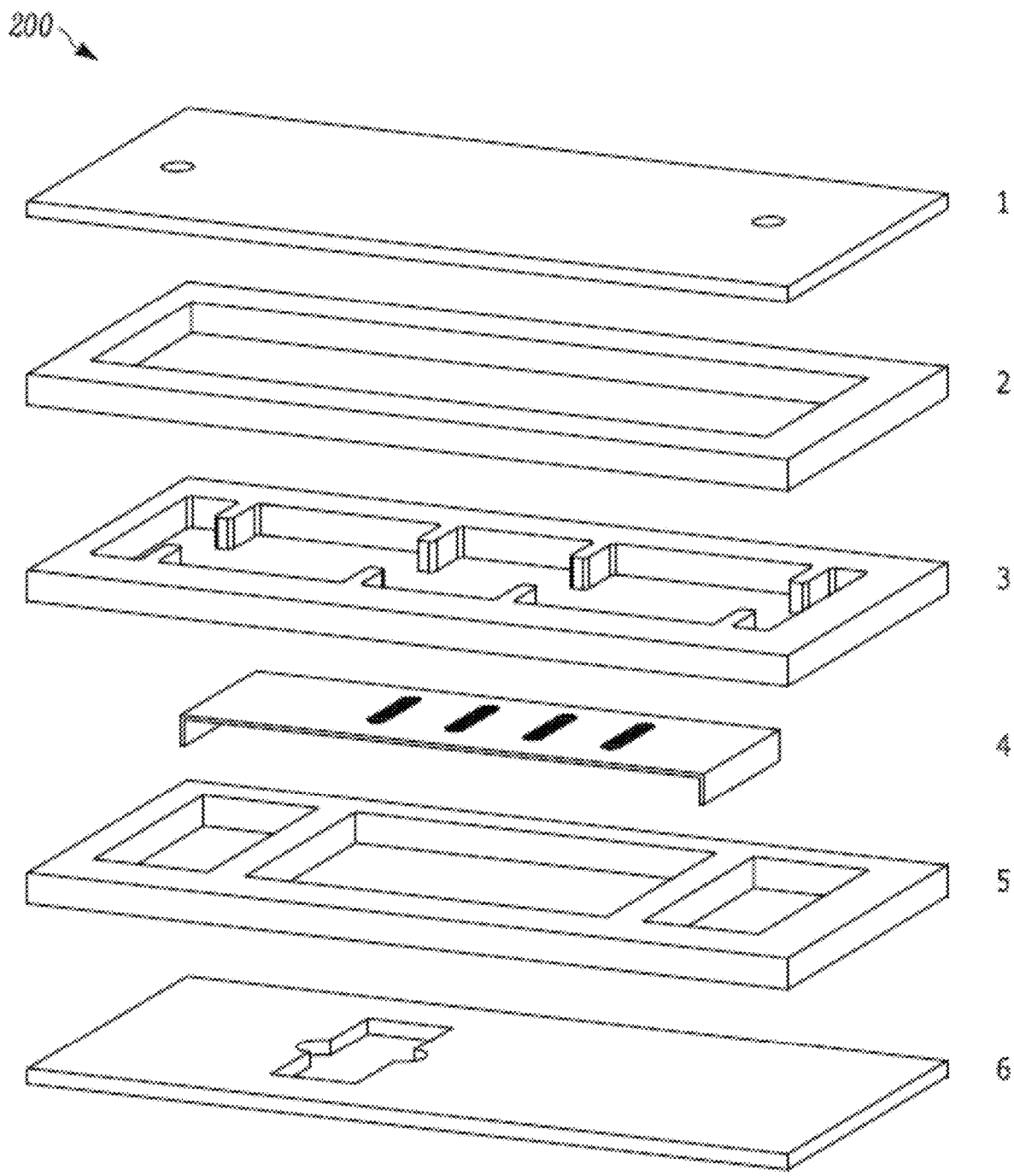
FIGS. 8A-8E illustrate another example cartridge electrophoresis device.

A HemeChip for diagnosis of hemoglobin disorders, including diabetes, was fabricated with multiple layer lamination of PMMA encompassing a single strip of cellulose acetate paper (FIG. 8A). In particular, poly (methyl methacrylate) (PMMA) sheets of 1.5 mm thickness were purchased from McMaster-Carr (Elmhurst, Ill.), and 1/32" thick PMMA sheets were purchased from ePlastics (San Diego, Calif.). 3M optically clear double sided adhesive (DSA) (Type 8142) was purchased from iTapeStore (Scotch Plains, N.J.).

Cellulose acetate membranes were purchased from Apacor and distributed by VWR International LLC (Radnor, Pa.). A 300V power supply was purchased from VWR International LLC (Model 302, Radnor, Pa.). Ponceau S Stain, Hemoglobin AFSC control, and Super Z microapplicator were purchased from Helena Laboratories (Beaumont, Tex.). Acetic acid glacial was purchased from Fisher Scientific (Waltham, Mass.). Graphite electrodes (0.9 mm) were purchased from Amazon (Seattle, Wash.). Black ⅛" diameter dots were purchased from Mark-It (Tonawanda, N.Y.).

HemeChip Fabrication and Assembly

Figure 8B:
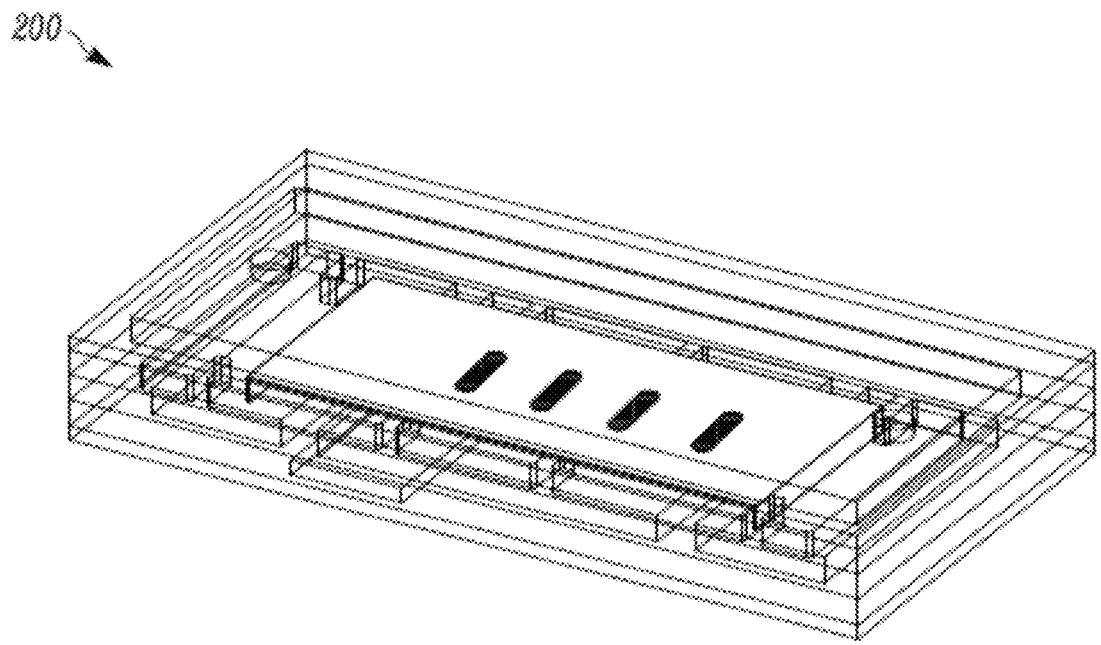

The DSA was used to assemble 5 layers of PMMA into a laminated, compact design (5 cm×2 cm×6 cm) capable of being carried in a pocket (FIG. 8B). We used the VersaLASER system (Universal Laser Systems Inc., Scottsdale, Ariz.), a laser micromachining system, for making individual PMMA layers as well as the DSA to attach the layers. The top and bottom layer of the HemeChip is made of ¹⁄₃₂" thick PMMA sheet, and the rest of the layers are made of 1.5 mm thick PMMA sheet. The DSA has a thickness of 50 μm. The cellulose acetate paper for the experiments is also cut (39 mm×9 mm) using the VersaLASER system. We have also fabricated a sample loading unit for the HemeChip using a similar manufacturing method with PMMA. The unit was compared to manual stamping by hand through analysis of the cross sectional area and repeatability of the blood sample application.

Figure 8C:
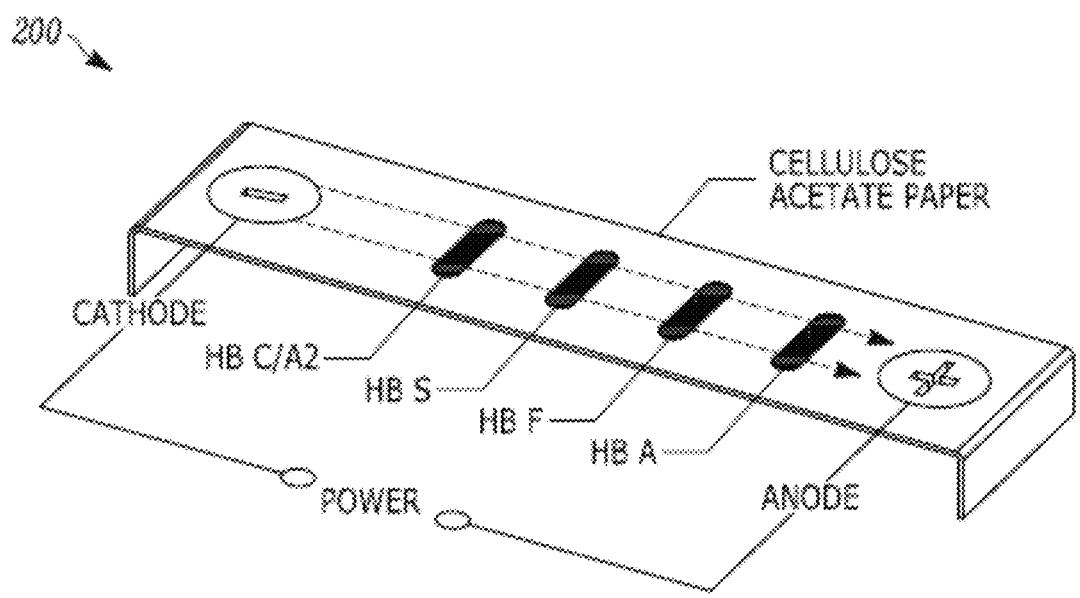
Figure 8D:
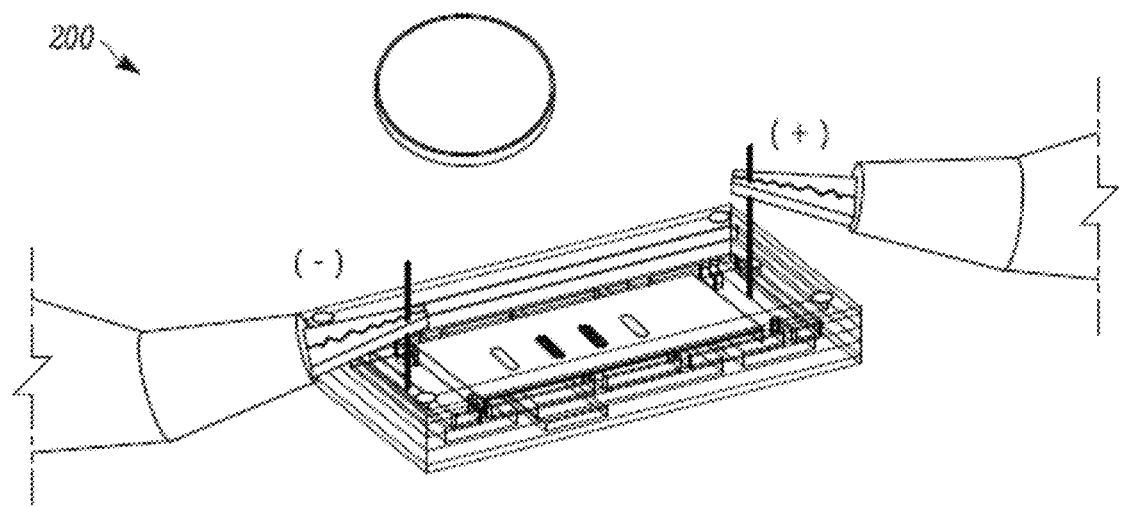
Figure 8E:
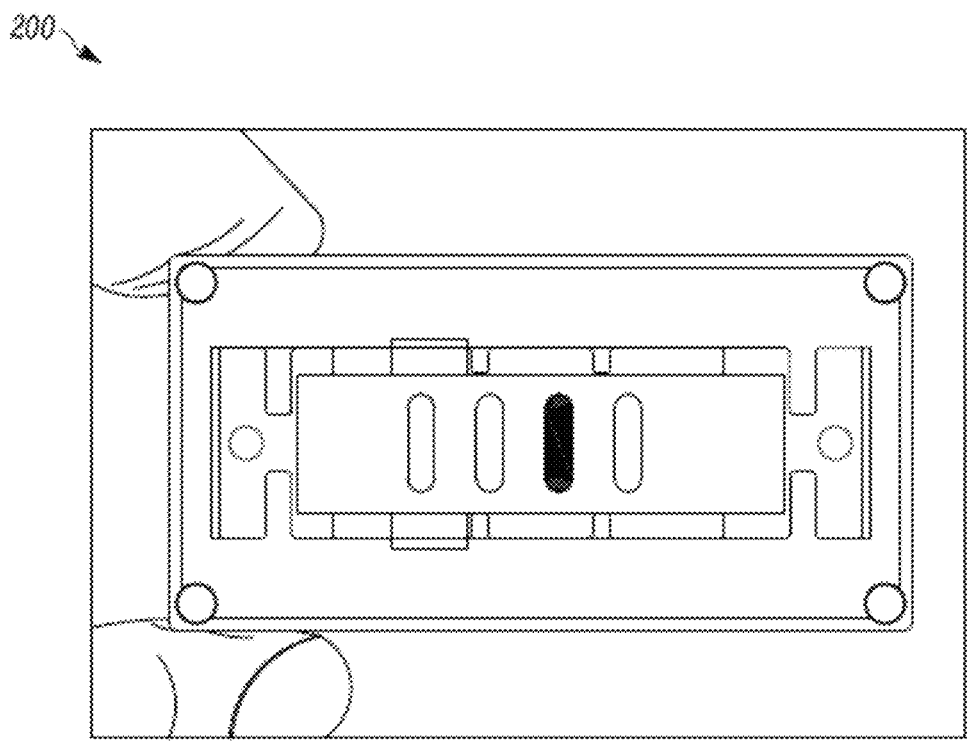

The CAD designs for the HemeChip were drawn using the CorelDRAW Suite X6 (Corel Corporation, Ottawa, Ontario) and SolidWorks 3D CAD (Waltham, Mass.). The designs were exported to the interface for VersaLASER system for making those layers. The cutting power for the VersaLASER system was prepped by setting the "vector cutting" from the intensity adjustment for the laser. The PMMA sheets and the DSA were cut with a setting of 45% (min: −50%, max: 50%) for the "vector cutting". We used a setting of −40% for cutting the cellulose acetate paper. A non-through cut at the both ends of the plastic back of the cellulose paper was created for bending the paper (FIG. 8C). The bending facilitates the buffer solution and paper contact for the electrophoresis. The non-through cuts were created at 3.0 mm off the ends using a setting of 50% (min: −50%, max: 50%) of "Raster" setting at the intensity adjustment for the laser.

Blood Preparation

Under Institutional Review Board (IRB) approval, discarded and de-identified patient blood samples were obtained from University Hospital's Hematology and Oncology Division (Cleveland, Ohio). Blood samples were collected into Vacutainer tubes containing EDTA anticoagulants (BD, Franklin Lakes, N.J.). Whole blood samples were stored standing at 10° C. and left to separate into plasma and hematocrit via gravity. The hematocrit of each sample was mixed with deionized water in a 1:5 ratio and placed on an ice block for 15 minutes to lyse the red blood cells. Prepared samples were stored in individual sealed microtubes at 10° C. and mixed gently before use. Samples were used and stored up to two weeks from the date received. Alternatively, whole blood samples can be lysed on the chip with a 1% Saponin+TBE buffer solution.

HemeChip Analysis

The cellulose acetate paper was soaked with 40 μL of buffer solution that includes 33 mmol citrate, 2 μmol dextran sulfate, and 8 μmol disodium EDTA per liter, at a pH of 6.4 via pipette through the HemeChip's sample loading port until fully saturated by capillary action. Excess buffer was left to dry or redistribute through the paper for 5 minutes. Less than 1 μL of prepared blood sample was stamped onto the paper using a micro-applicator through the sample loading port. Approximately 200 μL of buffer was pipetted into each buffer port. Graphite electrodes (1 inch length) were placed vertically into the buffer ports. The HemeChip was run at a constant voltage of 250V and max current of 5 mA for 8 minutes using a compact power supply. Optionally, Ponceau S stain (25 μL) was pipetted on to the paper and left to soak for 5 minutes. A 5% acetic acid wash was used to remove the stain until the hemoglobin bands were visible and the paper returned to its original white color. Four black ⅛" diameter dots were placed at each corner for use with the mobile and web-based image processing software.

Image Processing

A Nikon D3200 camera with a 40 mm f/2.8G AF-S DX Micro NIKKOR lens (Tokyo, Japan) was used to capture close up pictures of each HemeChip. Images were processed using ImageJ version 1.48 for Windows with no additional plugins. In each image, only the paper was cropped and used for analysis. The Subtract Background feature was used to apply a "rolling ball" algorithm with a radius of 25 pixels to remove smooth continuous background noise from the paper. The Plot Profile, Surface Plot, and Gel Plot tools were used to visualize and quantify the hemoglobin bands.

The Plot Profile tool provided the relative pixel intensities along the paper and were used to identify the peaks corresponding to each type of hemoglobin band. The area under each peak was calculated using the Gel Plot tools and represented the relative hemoglobin percentages (see for example FIG. 10). The area of each peak was outlined using the valley-to-valley method commonly used in gas chromatography. 3D Surface profiles of hemoglobin bands were obtained with the Surface Plot tool. Band distances were calculated in MATLAB to identify the coordinates of each peak on the profile plot. These were converted from pixels to mm using the HemeChip length-to-pixel ratio obtained from ImageJ. The same procedure was used to quantify the hemoglobin results from the standard benchtop electrophoresis setup.

Web-Based Image Processing and Quantification

Image processing algorithm: In this example the image processing algorithm is developed using MATLAB software and shown generally at 300 in FIG. 10. Briefly, the algorithm first reads the color image, detects the reference points and calibrates the image dimensions of the chip and the channel. Then the algorithm identifies the changes in red, blue and green values for each pixel along a reference line placed in the middle of the channel. This identification leads to detection of the peak values, which correspond to the reddish areas in the channel. Once the reddish areas are determined, the area of each area and the displacement from the start point is calculated. The area and the distance are used to determine the type of hemoglobin disease.

In order to have an image analysis system that is independent from the mobile operating systems, we designed the image-processing module compatible with cloud computing resources. As a result, any mobile device, which has a web browser and Internet connection, can be used to take image from HemeChip, transfer image to cloud computing servers for analysis and receive/display the results on the web browser.

We used MATLAB Compiler SDK™ (Software Development Kit) to produce a .dll file from the MATLAB code to process in .NET framework. The produced .dll file and Bootstrap framework were used to develop Asp.Net project. First, the webpage converts the image of HemeChip into mwArray object and transfers it to .NET library that runs the MATLAB code in the background. Then the output of the function produces another mwArray object and transfers back to the webpage for display. We are planning to increase the time efficiency of the image analysis by removing ASP.NET layer and integrating a fully scalable cloud computing system. In this design image-processing request will be conveyed to queuing service. Queuing service will distribute processing requests to Background Workers in order to execute the requests and scalability will be automatically performed based on the amount of requests. It is also possible to develop a mobile device application instead of running the analysis tool on the web browser. Having an application on the mobile device allows controlling camera features and taking calibrated HemeChip images.

Statistical Analysis

Band traveling distances for different hemoglobin types were statistically assessed (Minitab 16 software, Minitab Inc., State College, Pa.) using one way Analysis of Variance (ANOVA) test. The correlation and agreement between the measured hemoglobin concentrations for HemeChip and HPLC were evaluated using Pearson-product-moment correlation coefficient and Bland-Altman analysis. Limits of agreement in the Bland-Altman analysis were defined as the meant different ±1.96 times the standard deviation of the differences. Statistical significance was set at 95% confidence level for all tests (p<0.05). Receiver-operating curves were utilized to assess differentiation of different hemoglobin phenotypes based on their traveling distances in the HemeChip. Sensitivity was calculated as # true positives/(# true positives+# false negatives) and specificity was calculates as # true negatives/(# true negatives+# false positives). HemeChip data obtained in this study is reported as mean±standard deviation. Error bars in the figures represent the standard deviation.

Results

HemeChip was developed as the first miniaturized fully integrated single-use cartridge based microchip electrophoresis device for the detection and quantification of hemoglobin variants. HemeChip technology offers a timely, original and innovative solution, leveraging a novel engineering approach, to POC diagnosis of hemoglobinopathies (FIGS. 11A-E). HemeChip separates hemoglobin protein types in a minute volume of blood on a piece of cellulose acetate paper that is housed in a microengineered chip with a controlled environment and electric field (FIG. 11A-C). Differences in hemoglobin mobilities allow separation to occur within the cellulose acetate paper. The basis of HemeChip technology lies in hemoglobin electrophoresis in which hemoglobin types such as, A (normal), S (sickle), C (hemoglobin C disease), A2 (βthal, thalassemia), Bart's, and F (fetal) have net negative charges in an alkaline solution. Tris/Borate/EDTA (TBE) buffer is used to provide the necessary ions for electrical conductivity at a pH of 8.3. The overall negative net charges of the hemoglobins causes them to travel toward the positive electrode when placed in an electric field (FIG. 1C). Differences in hemoglobin mobilities allow separation to occur within the sieving medium, cellulose acetate. HemeChip is able to evaluate all the same variants as cellulose acetate electrophoresis, which is a standard test currently used in screening for hemoglobin disorders. One variation of cellulose acetate electrophoresis called affinity electrophoresis is used for the detection of glycosylated hemoglobin. This method utilizes an acidic buffer (pH 6.4) that exhibits an affinity to non-glycosylated hemoglobin, which facilitates its separation from glycosylated hemoglobin (FIG. 1D and FIGS. 2A&B), and can thus be used for A1C testing.

In our initial work aiming at validation of the cellulose acetate A1C testing, we ran tests with a benchtop electrophoresis system and cellulose acetate strips (Helena laboratories, Beaumont, Tex.). Two samples from normal subjects were tested. The cellulose acetate strips were stained and high-resolution colored images were taken. The software analyses data in real-time and the image analysis process can be broadly categorized in three stages: (i) image balance with background noise reduction, (ii) generation of intensity plot for peak detection, and (iii) calculation of area under the curve (AUC) for each detected peak to obtain relative percentages. ImageJ software was to perform the image analysis, in our proposed project, the image analysis procedure will be automated with a standalone application. The peaks identified and their relative percentages are shown in (FIG. 12A-B).

The sample is applied at the cathode and the hemoglobins migrate to the anode under the effect of the applied electric field. For the detection of Hemoglobin A1C, we will apply the principles of affinity electrophoresis which utilizes a buffer containing specific chemicals capable of interaction with specific hemoglobin types in the applied sample. For this purpose, we will use an affinity electrophoresis buffer consisting of 33 mmol citrate, 2 μmol dextran sulfate, and 8 μmol disodium EDTA per liter, at a pH of 6.4. Running electrophoresis with this buffer will take advantage of the affinity of the low-molecular mass dextran sulfate component for the non-glycosylated portion of the hemoglobin in the blood sample, which increases its mobility relative to the glycosylated hemoglobin. This difference in mobility will allow the separation and identification of the glycosylated hemoglobin.

Sample Preparation

Our current sample preparation steps include collection of a finger/heel prick blood sample, which is then mixed with DI water for a few minutes for lysis. The sample preparation for A1C detection will be slightly modified. Blood sample will have to be washed to purify the red blood cells before lysis, which is necessary to insure that the blood serum proteins do not interfere with the detection of the hemoglobin bands. Staining solution: A staining step might be necessary in this application to improve the visibility of the glycosylated hemoglobin band after separation (FIGS. 12A&B), and to improve the accuracy of the quantification results. The staining solution will be the commonly used Ponceau S. stain.

Modifications to the HemeChip Design

The current HemeChip design was scaled down from the benchtop electrophoresis setup. The design includes a 10×40 mm cellulose acetate strip (commercial system strips are 60×70 mm). This strip provides enough distance for the migration of all hemoglobin types detected in the screening of hemoglobin disorders (FIG. 11B), among which Hemoglobin A travels the largest distance. However, as the affinity electrophoresis employed for this application will cause the non-glycosylated hemoglobin A to move even further, the dimensions of the cellulose acetate strip will have to be modified to accommodate the new traveling distance. In addition to this change, we modified the microfluidic design of the chip to include a mechanism for introducing the stain and removing it when it has served its purpose.

Changes to the Electrophoretic Run Parameters

The affinity electrophoresis A1C detection procedures described in the literature for a large benchtop cellulose acetate electrophoresis system use 150 V run for 40 minutes. Since our HemeChip design is much smaller than the benchtop system these parameters will be scaled down. The voltage and current will be scaled based on the power and current densities needed to achieve good electrophoretic separation combined with a short run time.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, the following is claimed:

1. A diagnostic system for detecting hemoglobin, comprising:
   a cartridge including;
   a housing including a microchannel structured to receive a hemolysate of a blood sample, the microchannel extending between first and second buffer pools each containing about 1 μL to about 200 μL of a buffer solution, the buffer solution exhibiting an affinity to non-glycosylated hemoglobin, which facilitates its separation from glycosylated hemoglobin;
   an electrophoresis strip positioned within the microchannel and structured to receive at least a portion of a hemolysate, the electrophoresis strip having first and second ends positioned in the first and second buffer pools so as to be at least partially saturated with the buffer solution in each buffer pool;
   a first electrode connected to the housing and exposed to the buffer solution in the first buffer pool;
   a second electrode connected to the housing and exposed to the buffer solution in the second buffer pool, the first and second electrodes generating an electric field across the electrophoresis strip; and
   a sample loading port extending through the housing to the microchannel and providing access to a portion of the electrophoresis strip configured to receive hemolysate of the blood sample, the application of an electric field to the first and second electrodes inducing migration and separation of one or more bands of hemoglobin types in the sample delivered to the electrophoresis strip through the sample loading port; a portion of the housing being optically transparent for visualizing the one or more bands of migrated and separated hemoglobin types on the electrophoresis strip.

2. The diagnostic system of claim 1, wherein the cartridge further comprises a cover secured to the housing and including a projection aligned with the sample loading port and engaging the electrophoresis strip when the cover is connected to the housing for preventing movement of the electrophoresis strip during delivery of the sample to the electrophoresis strip.

3. The diagnostic system of claim 1, wherein the housing includes a first wall for delimiting the first buffer pool and a second wall for delimiting the second buffer pool, the first and second walls extending the entire width of the microchannel to prevent the buffer solution from flowing by capillary action out of each buffer pool.

4. The diagnostic system of claim 1 further comprising at least one first restricting member extending into the first buffer pool and at least one second restricting member extending into the second buffer pool, the first and second restricting members preventing longitudinal movement of the electrophoresis strip relative to the housing.

5. The diagnostic system of claim 4, wherein the electrophoresis strip has a length substantially equal to a distance between the at least one first restricting member and the at least one second restricting member.

6. The diagnostic system of claim 5, wherein the at least one first restricting member comprises a pair of first restricting members extending towards one another and parallel to the first wall, the at least one second restricting member comprising a pair of second restricting members extending towards one another and parallel to the second wall.

7. The diagnostic system of claim 1, wherein the first electrode is at least partially embedded in the first buffer pool and the second electrode is at least partially embedded in the second buffer pool.

8. The diagnostic system of claim 1, wherein the hemolysate of the blood sample introduced into the sample loading port is less than 10 μL.

9. The diagnostic system of claim 1, wherein the buffer solution is acidic and includes a sulfated polysaccharide.

10. The diagnostic system of claim 1 further comprising a power supply connected to the first electrode and the second electrode for supplying the electric field across the electrophoresis strip.

11. The diagnostic system of claim 1, further comprising an electrophoresis band detection module structured to detect the optically transparent portion of the housing the one or more bands of hemoglobin types on the electrophoresis strip caused by the applied electric field and to generate band detection data based on the one or more bands of migrated and separated hemoglobin types.

12. The diagnostic system of claim 11, further comprising a processor that receives and analyzes the band detection data to determine one or more band characteristics for each of the one or more bands of hemoglobin types and generate diagnostic results based on the one or more band characteristics.

13. The diagnostic system of claim 12, wherein the hemoglobin types comprise hemoglobin types $C/A_2$, S, F, $A_0$, A2, A1, and A1c.

14. The diagnostic system of claim 12, wherein the processor is configured to diagnose whether the subject has or is at risk of diabetes.

15. The diagnostic system of claim 12, wherein the electrophoresis strip defines an indicating member, the indicating member comprising a substantially U-shaped substrate in which the electrophoresis strip is embedded and indicia corresponding with the hemoglobin band types configured to self-calibrate the electrophoresis band detection module.

16. The diagnostic system of claim 1, wherein the cartridge is configured to introduce stain to the electrophoresis strip.

17. A diagnostic system for identification and quantification of glycosylated hemoglobin (HbA1c) and non-glycosylated hemoglobin (HbA) in a blood sample, the diagnostic system comprising:
   a cartridge including;
   a housing including a microchannel structured to receive a hemolysate of a blood sample, the microchannel extending between first and second buffer pools each containing about 1 μL to about 200 μL of a buffer solution, the buffer solution exhibiting an affinity to non-glycosylated hemoglobin, which facilitates its separation from glycosylated hemoglobin;
   an electrophoresis strip positioned within the microchannel and structured to receive at least a portion of a hemolysate, the electrophoresis strip having first and second ends positioned in the first and second buffer pools so as to be at least partially saturated with the buffer solution in each buffer pool;
   a first electrode connected to the housing and exposed to the buffer solution in the first buffer pool;
   a second electrode connected to the housing and exposed to the buffer solution in the second buffer pool, the first and second electrodes generating an electric field across the electrophoresis strip; and a sample loading port extending through the housing to the microchannel and providing access to a portion of the electrophoresis strip configured to receive hemolysate of the blood sample, the application of an electric field to the first and second electrodes inducing migration and separation of bands of HbA1c and HbA in the sample delivered to the electrophoresis strip through the sample loading port; a portion of the housing being optically transparent for visualizing the one or more bands of migrated and separated hemoglobin types on the electrophoresis strip;

an electrophoresis band detection module structured to detect through the optically transparent portion of the housing the HbA1 and HbA bands on the electrophoresis strip caused by the applied electric field and to generate band detection data based on the HbA1c and HbA bands; and a processor that receives and analyzes the band detection data to determine one or more band characteristics for each of the HbA1c and HbA bands and generate diagnostic results indicative of HbA1c and HbA in the blood sample.

18. The diagnostic system of claim 17, wherein the processor is configured to diagnose whether the subject has or is at risk of diabetes.

19. The diagnostic system of claim 17, wherein the buffer solution is acidic and includes a sulfated polysaccharide.

20. The diagnostic system of claim 17, wherein the cartridge is configured to introduce stain to the electrophoresis strip.

* * * * *